United States Patent

Otsuka et al.

Patent Number: 5,858,201
Date of Patent: Jan. 12, 1999

[54] STRONG ACID STERILIZING LIQUID CONTAINING HYPOCHLOROUS ACID AT A LOW CONCENTRATION, METHOD AND APPARATUS FOR GENERATING SAME, AND APPARATUS FOR GENERATING AND DISPENSING SAME

[75] Inventors: Toshiharu Otsuka; Toshio Eki; Akemi Takeshita; Hidetaka Miyahara; Sigeru Ando, all of Kitakyushu, Japan

[73] Assignee: Toto, Ltd., Kitakyushu, Japan

[21] Appl. No.: 776,388

[22] PCT Filed: Jul. 28, 1995

[86] PCT No.: PCT/JP95/01503

§ 371 Date: Jan. 28, 1997

§ 102(e) Date: Jan. 28, 1997

[87] PCT Pub. No.: WO96/03881

PCT Pub. Date: Feb. 15, 1996

[30] Foreign Application Priority Data

Jul. 29, 1994 [JP] Japan .................................. 6-196149
Aug. 19, 1994 [JP] Japan .................................. 6-216696
Aug. 19, 1994 [JP] Japan .................................. 6-216697

[51] Int. Cl.⁶ .................................................. C02F 1/461
[52] U.S. Cl. ......................... 205/701; 205/742; 205/556; 205/500; 204/228; 204/275
[58] Field of Search .................................. 205/701, 742, 205/556, 500; 204/275, 228

[56] References Cited

U.S. PATENT DOCUMENTS

| 3,819,329 | 6/1974 | Kaestner et al. ............................ 21/58 |
| 4,761,208 | 8/1988 | Gram et al. .............................. 205/701 |
| 4,783,246 | 11/1988 | Langeland et al. ...................... 205/500 |
| 5,308,507 | 5/1994 | Robson .................................. 205/701 |

FOREIGN PATENT DOCUMENTS

| A-1-317592 | 12/1989 | Japan . |
| A-2-111708 | 4/1990 | Japan . |
| A-6-321719 | 11/1994 | Japan . |
| A-7-118158 | 5/1995 | Japan . |
| A-7-187931 | 7/1995 | Japan . |

*Primary Examiner*—Arun S. Phasge
*Attorney, Agent, or Firm*—Griffin, Butler, Whisenhunt & Szipl, LLP

[57] ABSTRACT

A strong acid sterilizing liquid containing hypochlorous acid at a low concentration consists of electrolyzed salt water, wherein the pH of the liquid is 3 or less and the concentration of the hypochlorous acid is 0.2 ppm to 2 ppm.

54 Claims, 17 Drawing Sheets

STRONG ACID STERILIZING LIQUID CONTAINING HYPOCHLOROUS ACID AT A LOW CONCENTRATION, METHOD AND APPARATUS FOR GENERATING SAME, AND APPARATUS FOR GENERATING AND DISPENSING SAME

This application is a 371 of PCT/JP95/01503 filed Jul. 28, 1995.

TECHNICAL FIELD

The present invention relates to strong acid sterilizing liquid containing hypochlorous acid at a low concentration which is suitable for use on the human body, a method and an apparatus for generating strong acid sterilizing liquid containing hypochlorous acid at a low concentration, and an apparatus for generating and dispensing strong acid sterilizing liquid containing hypochlorous acid at a low concentration.

BACKGROUND ART

The bactericidal activity of an aqueous solution of hypochlorous acid varies with the pH of the solution because the state of chlorine compounds dissolved in the aqueous solution varies with pH.

When the pH of an aqueous solution of hypochlorous acid is 8 or more, or the aqueous solution of hypochlorous acid is alkaline, hypochlorous acid ions ($ClO^-$) having fairly low bactericidal activity are mainly present in the aqueous solution. Thus, the bactericidal activity of an alkaline aqueous solution of hypochlorous acid is fairly low.

When the pH of aqueous solution of hypochlorous acid is 7 or less, or the aqueous solution of hypochlorous acid is acidic, the amount of hypochlorous acid (HClO) which has bactericidal activity 10 to 100 times larger than that of hypochlorous acid ions, is larger than the amount of hypochlorous acid ions. Thus, the bactericidal activity of an acidic aqueous solution of hypochlorous acid is high.

When the pH of an aqueous solution of hypochlorous acid is 5.5 or less, substantially 100% of the chlorine compound dissolved in the aqueous solution is hypochlorous acid. Thus, the bactericidal activity of the aqueous solution of hypochlorous acid becomes even higher.

When the pH of an aqueous solution of hypochlorous acid is 3 or less, a part of the chlorine compound dissolved in the aqueous solution becomes chlorine gas ($Cl_2$) having higher bactericidal activity than that of hypochlorous acid. Thus, the bactericidal activity of the aqueous solution of hypochlorous acid becomes even higher.

Acid sterilizing liquid containing hypochlorous acid can instantly kill bacteria such as Escherichia coli, MRSA, Staphylococcus aureus, etc. Acid sterilizing liquid containing hypochlorous acid can cure inflamed parts of the human body suffering from atopy dermatitis, body parts suffering from necrosis owing to diabetes, and bedsores of a bedridden old person. It is thought that acid sterilizing liquid containing hypochlorous acid kills MRSA present on such diseased parts, in this way suppressing itch and suppuration of the parts and thereby curing them.

The skin is damaged by application of acid sterilizing liquid containing hypochlorous acid at a high concentration.

There is a need for an apparatus for generating and dispensing strong acid sterilizing liquid which contains hypochlorous acid at a concentration of about 2 ppm, the concentration prescribed by Japanese City Water Organization in its water purifier examination manual, whose pH is 3 or less, and which is suitable for use on the human body.

A continuously generating type apparatus having a barrier type electrolytic cell has been developed for generating acid liquid containing hypochlorous acid. In this apparatus, salt water is passed through a channel formed between a positive electrode plate and a negative electrode plate disposed to face opposite surfaces of a barrier membrane, and DC voltage is applied between the electrodes to electrolyze the salt water.

At the positive electrode, hydroxide ions ($OH^-$) contained in the salt water give electrons to the positive electrode to become oxygen gas and are eliminated from the water. Thus, the concentration of hydrogen ions ($H^+$) in the water flowing through the space between the barrier membrane and the positive electrode increases to make the water acidic. Also at the positive electrode, chlorine ions ($Cl^-$) contained in the salt water give electrons to the positive electrode to become chlorine gas ($Cl_2$). The chlorine gas dissolves in the acidic water to become hypochlorous acid.

At the negative electrode, hydrogen ions ($H^+$) contained in the salt water are given electrons from the negative electrode to become hydrogen gas and are eliminated from the water. Also at the negative electrode, sodium ions ($Na^+$) and hydroxide ions ($OH^-$) contained in the salt water are bonded together to become sodium hydroxide. Thus, the water flowing through the space between the barrier membrane and the negative electrode becomes alkaline.

The barrier membrane prevents the mixing of the products at the positive electrode and the products at the negative electrode. Acid liquid containing hypochlorous acid can be obtained by taking the water flowing through the space between the barrier membrane and the positive electrode out of the electrolytic cell.

The conventional continuously generating type apparatus for generating acid liquid containing hypochlorous acid having a barrier type electrolytic cell has a number of problems such as the following.

1. The conventional continuously generating type apparatus having a barrier type electrolytic cell cannot generate strong acid sterilizing liquid which contains hypochlorous acid at a concentration of about 2 ppm, whose pH is 3 or less, and which is suitable for use on the human body. The abbreviation "ppm" used here means concentration by weight converted into chlorine atoms and means "Cl mg/liter".

The inventors of the present invention studied why the conventional continuously generating type apparatus having a barrier type electrolytic cell cannot generate strong acid sterilizing liquid which contains hypochlorous acid at a concentration of about 2 ppm, whose pH is 3 or less, and which is suitable for use on the human body. Their conclusion was as follows.

When the pH of the electrolyzed water must be decreased, the electric current applied across the electrodes must be increased to increase the quantity of the electrolyzed salt water, thereby increasing the concentration of hydrogen ions in the electrolyzed water. Electrons are transferred between hydroxide ions, hydrogen ions and the electrodes at the surfaces of the electrodes. When the electric current is increased, the supply of hydroxide ions and hydrogen ions to the surfaces of the electrodes becomes insufficient, which suppresses the increase in the electric current.

When the voltage applied across the electrodes is increased to increase the supply of the hydroxide ions and hydrogen ions to the surfaces of the electrodes, overvoltage at the positive electrode increases and the generation of chlorine gas is promoted. Thus, the layer of the water flow near the positive electrode becomes strong acid liquid containing hypochlorous acid at a high concentration.

One countermeasure for overcoming the problem of the short supply of the hydroxide ions and hydrogen ions to the surfaces of the electrodes is to narrow the distance between the electrodes, thereby increasing the speed of the flow of the salt water through the channel between the electrodes. However, narrowing the distance between the electrodes is difficult because of the presence of the barrier membrane between the electrodes.

As can be seen from the foregoing explanation, a conventional continuously generating type apparatus having a barrier type electrolytic cell cannot generate strong acid sterilizing liquid which contains hypochlorous acid at a concentration of about 2 ppm, whose pH is 3 or less, and which is suitable for use on the human body.

Strong acid sterilizing liquid which is generated only by the electrolysis of salt water, which contains hypochlorous acid at a concentration of about 2 ppm, whose pH is 3 or less, and which is suitable for use on the human body has not been put to practical us, as described above, the conventional continuously generating type apparatus having a barrier type electrolytic cell cannot generate strong acid sterilizing liquid which contains hypochlorous acid at a concentration of about 2 ppm, whose pH is 3 or less, and which is suitable for use on the human body. According to a recent report, moreover, electrolyzed salt water which is diluted with nothing other than water, which contains hypochlorous acid at a concentration of about 2 ppm, and which is strongly acidic has hardly any bactericidal activity. This conclusion is based on tests using strong acid liquid containing hypochlorous acid at a low concentration which is obtained by adding sterilized distilled water to strong acid liquid containing hypochlorous acid at a high concentration generated by electrolysis of salt water, thereby diluting the strong acid liquid (Pharmacology and Clinical Medicine 1993/VOL.3/NO.9/SEP. page 71 table 1). The inventors of the present invention think that the reported lack of bactericidal activity arises because the hypochlorous acid was broken down into chlorine gas when the aqueous solution was diluted and the chlorine gas left the aqueous solution, thus reducing the bactericidal activity of the aqueous solution.

2. A barrier type electrolytic cell is large because of the presence of the barrier membrane between the electrodes. Thus, the conventional continuously generating type apparatus for generating acid liquid containing hypochlorous acid having a barrier type electrolytic cell is large and not portable. Conventionally, acid liquid containing hypochlorous acid generated in a continuously generating type apparatus having a barrier type electrolytic cell has therefore been stored in a tank and poured from the tank into a small vessel or sprayer for use. Hypochlorous acid is easily broken down by ultraviolet light and the chlorine component evaporates with the lapse of time. Thus, the bactericidal activity of the acid liquid containing hypochlorous acid decreases while it is stored in the tank.

3. Inflammation owing to atopy dermatitis often appears at a hidden part of the body. Therefore, it is preferable to provide an apparatus for generating and dispensing acid liquid containing hypochlorous acid which can be used in a bathroom. In a conventional continuously generating type apparatus having a barrier type electrolytic cell, the space between the electrodes is wide, about 4 mm or greater, owing to the presence of the barrier membrane between the electrodes, the electric resistance of the salt water present between the electrodes is large, and a large amount of electric power is needed to electrolyze the salt water. Thus, a conventional continuously generating type apparatus having a barrier type electrolytic cell has to be driven by domestic AC line current. However, AC line current is not ordinarily available in a bathroom. Thus, an apparatus for generating and dispensing acid liquid containing hypochlorous acid based on a conventional continuously generating type apparatus for generating acid liquid containing hypochlorous acid having a barrier type electrolytic cell cannot be used in a bathroom.

SUMMARY OF THE INVENTION

Through an extensive study, the inventors discovered that strong acid liquid which contains hypochlorous acid at a concentration of about 2 ppm, whose pH is 3 or less, and which is suitable for use on the human body can be obtained by electrolyzing salt water using a continuously generating type apparatus having a non-barrier type electrolytic cell, and further ascertained that the obtained strong acid liquid has strong bactericidal activity.

The present invention was made based on this discovery. Therefore, an object of the present invention is to provide a method and an apparatus for generating strong acid sterilizing liquid containing hypochlorous acid at a low concentration which can be used for treating the human body.

Another object of the present invention is to provide a small sized portable type apparatus for generating and dispensing strong acid sterilizing liquid containing hypochlorous acid at a low concentration, wherein the dispensed strong acid sterilizing liquid has reliable bactericidal activity. Another object of the present invention is to provide an apparatus for generating and dispensing strong acid sterilizing liquid containing hypochlorous acid at a low concentration, which does not need a large amount of electric power for the electrolysis of salt water and can be driven by a battery.

In accordance with the present invention, there is provided strong acid sterilizing liquid containing hypochlorous acid at a low concentration consisting of electrolyzed salt water, wherein the pH of the liquid is 3 or less and the concentration of the hypochlorous acid is 0.2 ppm to 2 ppm.

In the sterilizing liquid of the present invention whose pH is 3 or less, chlorine compounds exist in the state of hypochlorous acid and partially as chlorine gas. Thus, the sterilizing liquid of the present invention has a strong bactericidal activity. The sterilizing liquid of the present invention wherein the concentration of the hypochlorous acid is 0.2 ppm to 2.0 ppm is harmless when applied to the human body and is suitable for use on the human body. In the sterilizing liquid of the present invention which consists of electrolyzed salt water only and is not diluted with distilled water etc., the hypochlorous acid contained in the sterilizing liquid can exist stably. Thus, the sterilizing liquid of the present invention has reliable bactericidal activity.

In accordance with another aspect of the present invention, there is provided a method for generating strong acid sterilizing liquid containing hypochlorous acid at a low concentration comprising the steps of forming a channel by a pair of flat wall surfaces extending close to, parallel to, and opposite to each other without a barrier membrane between them, constituting at least a part of one of the pair of wall surfaces of a positive electrode plate, constituting at least a part of the other of the pair of wall surfaces of a negative electrode plate, passing salt water through the channel, electrolyzing the salt water flowing through the channel, and taking a layer of the water flow along the wall surface a part of which is constituted of the positive electrode plate out of the downstream portion of the channel through an outlet port formed in the wall surface a part of which is constituted of the positive electrode plate.

In accordance with another aspect of the present invention, there is provided a method for generating strong acid sterilizing liquid containing hypochlorous acid at a low concentration comprising the steps of forming a channel by a pair of flat wall surfaces extending close to, parallel to, and opposite to each other without a barrier membrane between them, constituting at least a part of one of the pair of wall surfaces of a positive electrode plate, constituting at least a part of the other of the pair of wall surfaces of a negative electrode plate, passing salt water through the channel, electrolyzing the salt water flowing through the channel, and taking the layer of the water flow along the wall surface a part of which is constituted of the negative electrode plate away from the downstream portion of the channel through an outlet port formed in the wall surface a part of which is constituted of the negative electrode plate.

In the method for generating strong acid sterilizing liquid containing hypochlorous acid at a low concentration in accordance with the present invention, the positive electrode and the negative electrode are disposed opposite to each other without a barrier membrane between them. Thus, the distance between the electrodes can be made narrower than that in the conventional method using a barrier type electrolytic cell. This makes it possible to increase the flow speed of the salt water through the channel between the electrodes and thereby increase the number of hydroxide ions and hydrogen ions supplied to the surfaces of the electrodes. Thus, in the present method, strong acid electrolyzed water can be obtained with suppressing the increase of the voltage applied across the electrodes and thereby suppressing the generation of hypochlorous acid. In the method according to the present invention, salt water flowing through the channel constituted by a pair of flat wall surfaces extending close to, parallel to, and opposite to each other forms a laminar flow. Thus, the layer of the strong acid water flow along the wall surface a part of which is constituted by the positive electrode does not mix with the layer of the strong alkaline water flow along the wall surface a part of which is constituted by the negative electrode.

In the method according to the present invention, the layer of the water flow along the wall surface a part of which is constituted by the positive electrode plate is taken out of the downstream portion of the channel through an outlet port formed in the wall surface a part of which is constituted by the positive electrode plate, or the layer of the water flow along the wall surface a part of which is constituted by the negative electrode plate is taken away from the downstream portion of the channel through an outlet port formed in the wall surface a part of which is constituted by the negative electrode plate. Thus, strong acid sterilizing liquid containing hypochlorous acid at a low concentration is obtained.

In accordance with a preferred embodiment of the present invention, the distance between the wall surfaces is 0.5 mm or less.

When the distance between the wall surfaces is 0.5 mm or less, the water flow in the channel between the electrodes becomes laminar flow.

In accordance with another preferred embodiment of the present invention, the electric power for the electrolysis is variably controlled.

In accordance with another preferred embodiment of the present invention, the concentration of salt in the salt water is variably controlled.

When the electric power for the electrolysis is variably controlled, or the concentration of salt in the salt water is variably controlled, strong acid sterilizing liquid containing hypochlorous acid at a low concentration having a desired pH value and concentration of hypochlorous acid is obtained.

In accordance with another aspect of the present invention, there is provided an apparatus for generating strong acid sterilizing liquid containing hypochlorous acid at a low concentration comprising an electrolytic cell having a first channel formed between a pair of flat wall surfaces extending close to, parallel to, and opposite to each other without a barrier membrane between them, a positive electrode plate constituting at least a part of one of the pair of wall surfaces, a negative electrode plate constituting at least a part of the other of the pair of wall surfaces, a second channel for taking out strong acid liquid communicating with the downstream portion of the first channel through an outlet port formed in the wall surface a part of which is constituted of the positive electrode plate, a third channel for taking out strong alkaline liquid communicating with the downstream end of the first channel, and a fourth channel for supplying salt water communicating with the upstream end of the first channel; a salt water tank communicating with the fourth channel of the electrolytic cell; and a DC power supply for applying voltage across the positive electrode plate and the negative electrode plate.

In accordance with another aspect of the present invention, there is provided an apparatus for generating strong acid sterilizing liquid containing hypochlorous acid at a low concentration comprising an electrolytic cell having a first channel formed between a pair of flat wall surfaces extending close to, parallel to, and opposite to each other without a barrier membrane between them, a positive electrode plate constituting at least a part of one of the pair of wall surfaces, a negative electrode plate constituting at least a part of the other of the pair of wall surfaces, a second channel for taking out strong alkaline liquid communicating with the downstream portion of the first channel through an outlet port formed in the wall surface a part of which is constituted of the negative electrode plate, a third channel for taking out strong acid liquid communicating with the downstream end of the first channel, and a fourth channel for supplying salt water communicating with the upstream end of the first channel; a salt water tank communicating with the fourth channel of the electrolytic cell; and a DC power supply for applying voltage across the positive electrode plate and the negative electrode plate.

In the apparatus for generating strong acid sterilizing liquid containing hypochlorous acid at a low concentration in accordance with the present invention, salt water is supplied to the first channel from the salt water tank through the fourth channel. The DC power supply applies DC voltage across the positive electrode plate constituting at least a part of one of the pair of wall surfaces forming the first channel and the negative electrode plate constituting at least a part of the other of the pair of wall surfaces forming the first channel so as to electrolyze the salt water flowing through the first channel between the positive electrode plate and the negative electrode plate. The acid water containing hypochlorous acid generated near the positive electrode and flowing along the wall surface of the first channel a part of which is constituted by the positive electrode plate passes into the second channel from the downstream portion of the first channel through the outlet port formed in the wall surface a part of which is constituted by the positive electrode plate and is taken out of the electrolytic cell, or the alkaline water flowing along the wall surface of the first channel a part of which is constituted by the negative electrode plate passes into the second channel from the downstream portion of the first channel through the outlet port formed in the wall surface a part of which is constituted by the negative electrode plate and is taken away, and thereafter, the acid water containing hypochlorous acid flowing along the wall surface of the first channel a part of which is constituted by the positive electrode plate passes into the third channel from the downstream end of the first channel and is taken out of the electrolytic cell.

In the apparatus for generating strong acid sterilizing liquid containing hypochlorous acid at a low concentration in accordance with the present invention, the positive electrode plate and the negative electrode plate are disposed opposite to each other without a barrier membrane between them. Thus, the space between the electrodes can be made narrower than that in the conventional apparatus having a barrier type electrolytic cell. This makes it possible to increase the flow speed of the salt water through the first channel between the electrodes and thereby increase the number of hydroxide ions and hydrogen ions supplied to the surfaces of the electrodes. Thus, strong acid electrolyzed water can be obtained with suppressing the increase of the voltage applied across the electrodes and thereby suppressing the generation of hypochlorous acid. In the apparatus according to the present invention, saltwater flowing through the first channel constituted by a pair of flat wall surfaces extending close to, parallel to, and opposite to each other forms a laminar flow. Thus, the layer of the strong acid water flow along the wall surface a part of which is constituted by the positive electrode plate does not mix with the layer of the strong alkaline water flow along the wall surface a part of which is constituted by the negative electrode plate. In the apparatus according to the present invention, the layer of the water flow along the wall surface a part of which is constituted by the positive electrode plate is taken out of the downstream portion of the first channel through an outlet port formed in the wall surface a part of which is constituted by the positive electrode plate, or the layer of the water flow along the wall surface a part of which is constituted by the negative electrode plate is taken away from the downstream portion of the first channel through an outlet port formed in the wall surface a part of which is constituted of the negative electrode plate, and thereafter, the layer of the water flow along the wall surface a part of which is constituted by the positive electrode plate is taken out of the downstream end of the first channel. Thus, strong acid sterilizing liquid containing hypochlorous acid at a low concentration is obtained.

In accordance with a preferred embodiment of the present invention, the distance between the wall surfaces constituting the first channel is 0.5 mm or less.

When the distance between the wall surfaces constituting the first channel is 0.5 mm or less, the water flow in the first channel between the electrodes becomes laminar flow.

In accordance with another preferred embodiment of the present invention, the apparatus for generating strong acid sterilizing liquid containing hypochlorous acid at a low concentration further has a controller for variably controlling electric power for the electrolysis.

In accordance with another preferred embodiment of the present invention, the apparatus for generating strong acid sterilizing liquid containing hypochlorous acid at a low concentration further has a controller for variably controlling the concentration of salt in the salt water .

When the electric power for the electrolysis is variably controlled, or the concentration of salt in the salt water is variably controlled, strong acid sterilizing liquid containing hypochlorous acid at a low concentration having a desired pH value and concentration of hypochlorous acid is obtained.

In accordance with another aspect of the present invention, there is provided an apparatus for generating and dispensing strong acid sterilizing liquid containing hypochlorous acid at a low concentration comprising a non-barrier type electrolytic cell, a salt water tank, a discarded water recovery tank, means for force feeding salt water from the salt water tank to the non-barrier type electrolytic cell, a DC power supply, and a controller, wherein the non-barrier type electrolytic cell has a water flow channel formed between a pair of flat wall surfaces extending close to, parallel to, and opposite to each other without a barrier membrane between them, a positive electrode plate constituting at least a part of one of the pair of wall surfaces, a negative electrode plate constituting at least a part of the other of the pair of wall surfaces, an acid liquid recovery channel communicating with the downstream portion of the water flow channel through an outlet port formed in the wall surface a part of which is constituted of the positive electrode plate, an alkaline liquid recovery channel communicating with the downstream end of the water flow channel, and a salt water supply channel communicating with the upstream end of the water flow channel, and wherein the salt water supply channel communicates with the salt water tank, the alkaline liquid recovery channel communicates with the discarded water recovery tank, and the acid liquid recovery channel communicates with an acid liquid discharge port.

In accordance with another aspect of the present invention, there is provided an apparatus for generating and dispensing strong acid sterilizing liquid containing hypochlorous acid at a low concentration comprising a non-barrier type electrolytic cell, a salt water tank, a discarded water recovery tank, means for force feeding salt water from the salt water tank to the non-barrier type electrolytic cell, a DC power supply, and a controller, wherein the non-barrier type electrolytic cell has a water flow channel formed between a pair of flat wall surfaces extending close to, parallel to, and opposite to each other without a barrier membrane between them, a positive electrode plate constituting at least a part of one of the pair of wall surfaces, a negative electrode plate constituting at least a part of the other of the pair of wall surfaces, an acid liquid recovery channel communicating with the downstream end of the water flow channel, an alkaline liquid recovery channel communicating with the downstream portion of the water flow channel through an outlet port formed in the wall surface a part of which is constituted of the negative electrode plate, and a salt water supply channel communicating with the upstream end of the water flow channel, and wherein the salt water supply channel communicates with the salt water tank, the acid liquid recovery channel communicates with an acid liquid discharge port, and the alkaline recovery channel communicates with the discarded water recovery tank.

In the apparatus for generating and discharging strong acid sterilizing liquid containing hypochlorous acid at a low concentration in accordance with the present invention, the salt water stocked in the salt water tank is fed to the non-barrier type electrolytic cell by the force feeding means.

The salt water flows into the salt water supply channel of the non-barrier type electrolytic cell and, thereafter, into the water flow channel. The DC power supply applies DC voltage across the positive electrode plate constituting at least a part of one of the pair of wall surfaces forming the water flow channel and the negative electrode plate constituting at least a part of the other of the pair of wall surfaces forming the water flow channel so as to electrolyze the salt water flowing through the water flow channel between the positive electrode plate and the negative electrode plate. Acid liquid containing hypochlorous acid generated near the positive electrode and flowing along the wall surface of the water flow channel a part of which is constituted by the positive electrode plate passes into the acid liquid recovery channel from the downstream portion of the water flow channel through the outlet port formed in the wall surface a part of which is constituted by the positive electrode plate, and is discharged from the acid liquid discharge port, or alkaline liquid flowing along the wall surface of the water flow channel a part of which is constituted by the negative electrode plate passes into the alkaline liquid recovery channel from the downstream portion of the water flow channel through the outlet port formed in the wall surface a part of which is constituted by the negative electrode plate and is taken away, and thereafter, acid liquid containing hypochlorous acid flowing along the wall surface of the water flow channel a part of which is constituted by the positive electrode plate passes into the acid liquid recovery channel from the downstream end of the water flow channel and is discharged from the acid liquid discharge port. The alkaline liquid taken away from the non-barrier type electrolytic cell flows into the discarded water recovery tank. The controller controls the operations of the force feeding means and the non-barrier type electrolytic cell.

In the apparatus for generating strong acid sterilizing liquid containing hypochlorous acid at a low concentration in accordance with the present invention, the positive electrode plate and the negative electrode plate are disposed opposite to each other without a barrier membrane between them. Thus, the distance between the electrodes can be made narrower than that in the conventional apparatus having a barrier type electrolytic cell. This makes it possible to decrease the electric resistance of the salt water present between the electrodes, whereby the salt water can be electrolyzed with less consumption of electric power. Thus, in the present invention, the non-barrier type electrolytic cell can be made compact by means of narrowing the distance between the electrodes, the DC power supply and the controller can be made compact by means of reducing the consumption of electric power, and the whole apparatus can be made compact and portable. Since the present apparatus is compact and portable, users can freely take it to a desired place where they want to use it. Thus, the present apparatus has high utility. With the present apparatus having a compact non-barrier type electrolytic cell, it is possible to generate only the necessary quantity of the strong acid sterilizing liquid containing hypochlorous acid at a low concentration and immediately use up the generated strong acid sterilizing liquid. As the generated strong acid sterilizing liquid containing hypochlorous acid at a low concentration is immediately used up, the strong acid sterilizing liquid containing hypochlorous acid at a low concentration has reliable bactericidal activity.

In the apparatus for generating strong acid sterilizing liquid containing hypochlorous acid at a low concentration in accordance with the present invention, the space between the electrodes can be made narrow to decrease the voltage applied across the electrodes, thereby decreasing the overvoltage at the positive electrode, increase the flow speed of the salt water through the water flow channel between the electrodes, thereby increasing the number of hydroxide ions and hydrogen ions supplied to the surfaces of the electrodes, and cause the water flow through the water flow channel to be a laminar flow. Thus, in the present apparatus, electrolysis of the salt water can be promoted, while suppressing excessive generation of chlorine and suppressing mixing of the water flow near the positive electrode and the water flow near the negative electrode, whereby strong acid sterilizing liquid which contains hypochlorous acid at a concentration of about 2 ppm, whose pH is 3 or less, and which is suitable for use on the human body can be obtained.

In the apparatus for generating and discharging strong acid sterilizing liquid containing hypochlorous acid at a low concentration in accordance with the present invention, the distance between the positive electrode plate and the negative electrode plate can be made narrow to decrease the voltage and the electric power required for the electrolysis. Thus, in the present apparatus, a battery can be used as the power supply for the electrolysis.

In accordance with a preferred embodiment of the present invention, the distance between the positive electrode plate and the negative electrode plate of the non-barrier type electrolytic cell is about 0.2 mm to about 0.5 mm.

When the distance between the positive electrode plate and the negative electrode plate of the non-barrier type electrolytic cell is about 0.2 mm to about 0.5 mm, a battery can be used as the power supply for the electrolysis, the non-barrier type electrolytic cell can be made small to reduce the quantity of the liquid discharged at the start of the operation of the apparatus and having no bactericidal activity, and the flow resistance of the water flow channel can be optimized to enable use of a battery as the power supply for the force feeding means.

In accordance with a preferred embodiment of the present invention, the ratio of the sectional area of the channel for communicating the salt water supply channel with the salt water tank to that of a channel for communicating the alkaline liquid recovery channel with the discarded water recovery tank is 2 to 1.

When the ratio of the sectional area of the channel for communicating the salt water supply channel with the salt water tank to that of a channel for communicating the alkaline liquid recovery channel with the discarded water recovery tank is 2 to 1, the flow of the salt water and the alkaline liquid in the channels can be made smooth.

In accordance with a preferred embodiment of the present invention, an electrolytic cell unit of palm size is constituted by the non-barrier type electrolytic cell, a base unit is constituted by the salt water tank, the discarded water recovery tank, the means for force feeding salt water from the salt water tank to the non-barrier type electrolytic cell, the DC power supply and the controller, the electrolytic cell unit is connected to the base unit through a harness having a salt water supply tube, a discarded water discharge tube and electric wires, the salt water supply channel communicates with the salt water supply tube of the harness, and the alkaline liquid recovery channel communicates with the discarded water discharge tube of the harness.

When an electrolytic cell unit of palm size is constituted by the non-barrier type electrolytic cell, a base unit is constituted by the salt water tank, the discarded water recovery tank, the means for force feeding salt water from the salt water tank to the non-barrier type electrolytic cell, the DC power supply and the controller, the electrolytic cell unit is connected to the base unit through a harness having a salt water supply tube, a discarded water discharge tube and electric wires, the salt water supply channel communicates with the salt water supply tube of the harness, and the alkaline liquid recovery channel communicates with the discarded water discharge tube of the harness, the user can grasp the palm sized electrolytic cell unit to directly apply the acid liquid containing hypochlorous acid to any part of his or her body or impregnate the acid liquid containing hypochlorous acid into absorbent cotton and apply it to any part of his or her body. Thus, the present apparatus has high utility.

In accordance with a preferred embodiment of the present invention, the base unit has a compartment for accommodating the electrolytic cell unit and the harness.

When the base unit has a compartment for accommodating the electrolytic cell unit and the harness, the whole apparatus becomes an integral body. Thus, downsizing and portability of the apparatus is promoted.

In accordance with a preferred embodiment of the present invention, the apparatus for generating and dispensing strong acid sterilizing liquid containing hypochlorous acid at a low concentration further has means for hooking the electrolytic cell unit on the base unit.

The means for hooking the electrolytic cell unit on the base unit enables the use of the present apparatus with the electrolytic cell unit hooked on the base unit. Thus, the user can impregnate the sterilizing liquid into absorbent cotton and apply it to diseased parts without picking up the electrolytic cell unit.

In accordance with a preferred embodiment of the present invention, the electrolytic cell unit has a hand switch connected to the controller of the base unit.

When the electrolytic cell unit has a hand switch connected to the controller of the base unit, the present apparatus can be easily handled.

In accordance with a preferred embodiment of the present invention, the means for force feeding salt water is a pump disposed in the middle of the channel for communicating the salt water supply channel with the salt water tank.

In accordance with a preferred embodiment of the present invention, the means for force feeding salt water is a compressor for pressurizing the liquid in the salt water tank.

When the means for force feeding salt water is a pump disposed in the middle of the channel for communicating the salt water supply channel with the salt water tank, or a compressor for pressurizing the liquid in the salt water tank, the salt water can be force fed from the salt water tank to the non-barrier type electrolytic cell without difficulty.

In accordance with a preferred embodiment of the present invention, a closing valve is disposed in the middle of the channel for communicating the salt water supply channel with the salt water tank.

When the means for force feeding salt water is a compressor for pressurizing the liquid in the salt water tank, the supply of the salt water to the non-barrier type electrolytic cell and the stopping of the supply of the salt water to the non-barrier type electrolytic cell is carried out by the closing valve disposed in the middle of the channel for communicating the salt water supply channel with the salt water tank.

In accordance with a preferred embodiment of the present invention, the apparatus in accordance with the present invention further has means for reversing the polarity of the voltage applied across the electrodes of the non-barrier type electrolytic cell.

Adhesion of scale to the electrode plates can be suppressed by reversing the polarity of the voltage applied across the electrodes of the non-barrier type electrolytic cell.

In accordance with a preferred embodiment of the present invention, ion exchange resin is disposed in the salt water tank.

Adhesion of scale to the negative electrode plate can be suppressed by removing calcium ions from the salt water by means of the ion exchange resin disposed in the salt water tank.

In accordance with a preferred embodiment of the present invention, the DC power supply is a battery type power supply.

When the DC power supply of the present apparatus is a battery type power supply, the present apparatus can be used in a bathroom.

In accordance with a preferred embodiment of the present invention, the acid liquid discharge port is connected to a sprayer.

When the acid liquid discharge port is connected to a sprayer, the strong acid sterilizing liquid can be sprayed. Thus, an appropriate quantity of strong acid sterilizing liquid can be applied to the diseased part.

In accordance with a preferred embodiment of the present invention, the sprayer has a piezoelectric element and a porous plate secured to the piezoelectric element at its one end.

When the sprayer is constituted by a piezoelectric element and a porous plate secured to the piezoelectric element at its one end, the sprayer can be downsized, electric power consumption of the sprayer can be reduced, and a battery can be used as the power supply of the sprayer.

In accordance with a preferred embodiment of the present invention, the porous plate is made of acid proof material.

In accordance with a preferred embodiment of the present invention, the whole surface of the porous plate including inner surfaces of the pores is coated with acid proof material.

When the porous plate is made of acid proof material, or the whole surface of the porous plate including inner surfaces of the pores is coated with acid proof material, the corrosion resistance of the porous plate to the strong acid sterilizing liquid containing hypochlorous acid at a low concentration can be increased.

In accordance with a preferred embodiment of the present invention, the sprayer has an open spray tank communicating with the acid water recovery channel of the non-barrier type electrolytic cell and the open end of the open spray tank is covered with the porous plate.

When the sprayer has an open spray tank communicating with the acid water recovery channel of the non-barrier type electrolytic cell and the open end of the open spray tank is covered with the porous plate, the strong acid sterilizing liquid containing hypochlorous acid at a low concentration flows into the open spray tank through the acid liquid recovery channel of the non-barrier type electrolytic cell, fills the open spray tank, rises to one surface of the porous plate, and is sprayed from the other surface of the porous plate through the numerous pores formed in the porous plate. The sterilizing liquid is supplied to one surface of the porous plate and sprayed from the other surface of the porous plate. Thus, the sterilizing liquid can be sprayed stably and in a good condition.

In accordance with a preferred embodiment of the present invention, the distance between the porous plate and the bottom of the open spray tank opposite to the porous plate is about 0.5 mm to about 1.5 mm.

When the distance between the porous plate and the bottom of the open spray tank opposite to the porous plate is about 0.5 mm to about 1.5 mm, the vibration of the porous plate is not stopped by adherence thereof to the bottom of the open spray tank due to the surface tension of the sterilizing liquid and is not suppressed due to increase of the added mass of water.

In accordance with a preferred embodiment of the present invention, the present apparatus whose acid liquid discharge port is connected to the sprayer further has means for continuing the spray until a prescribed time passes after the stop of the electrolysis.

When the present apparatus whose acid liquid discharge port is connected to the sprayer further has means for continuing the spray until a prescribed time passes after the stop of the electrolysis, the acid liquid containing hypochlorous acid residing in the sprayer and the channel for communicating the non-barrier type electrolytic cell with the sprayer can be used up at the end of the operation of the apparatus. Thus, the quantity of the liquid having no bactericidal activity which is discharged at the start of the next operation of the present apparatus can be reduced.

DESCRIPTION OF THE PREFERRED EMBODIMENTS

Preferred embodiments of the present invention will be described.

1. An Apparatus for Generating Strong Acid Sterilizing Liquid Containing Hypochlorous Acid at a Low Concentration.

Figure 1:
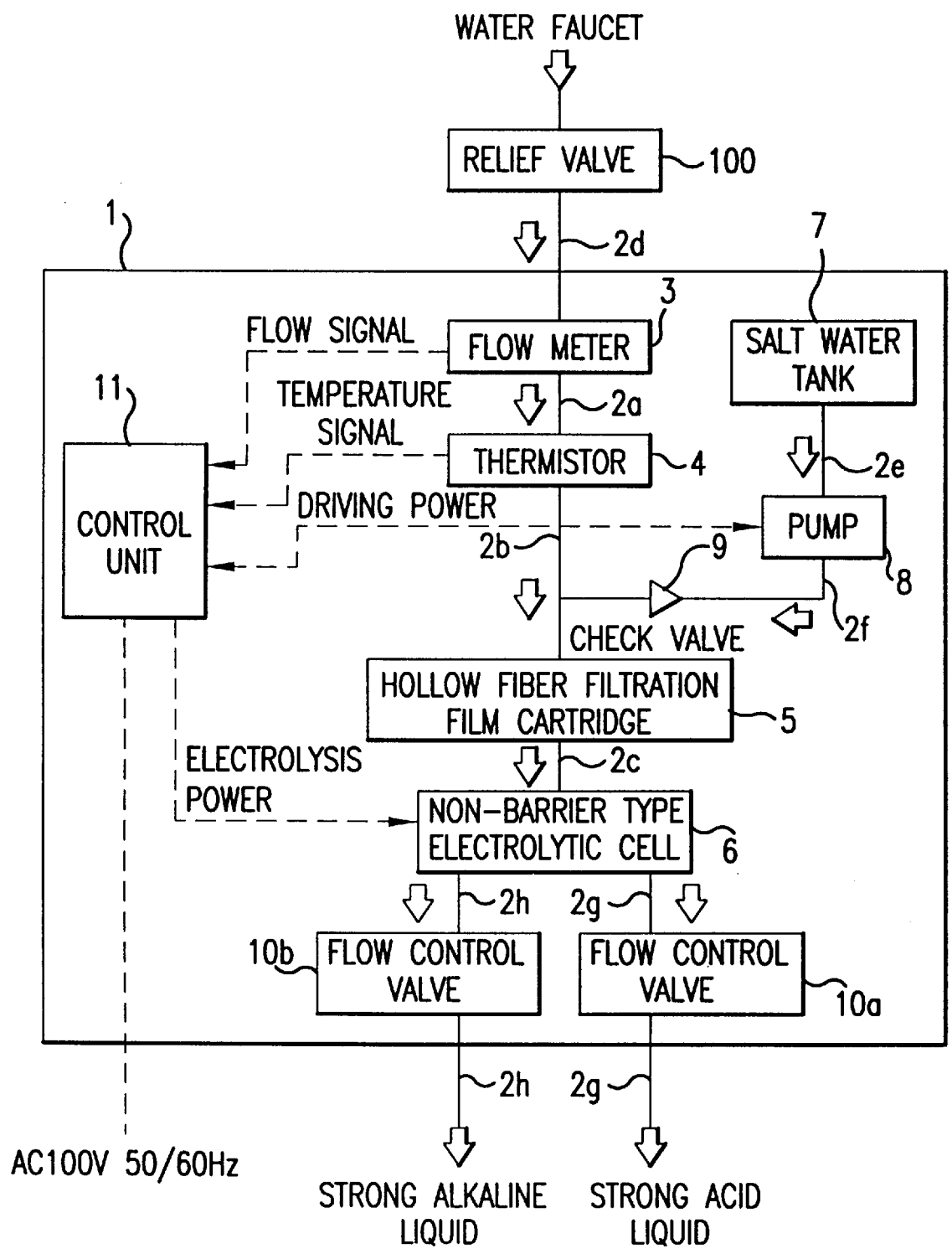
FIG. 1 is the layout of an apparatus for generating strong acid sterilizing liquid containing hypochlorous acid at a low concentration in accordance with an embodiment of the present invention.

As shown in FIG. 1, an apparatus 1 for generating strong acid sterilizing liquid containing hypochlorous acid at a low concentration in accordance with an embodiment of the present invention has a flow meter 3, a thermistor 4, a hollow fiber filtration film cartridge 5 and a non-barrier type electrolytic cell 6 which are connected in tandem by conduits 2a, 2b and 2c. A conduit 2d extends from the flow meter 3. A salt water tank 7 and a pump 8 are connected by a conduit 2e. The pump 8 is connected to the conduit 2b connecting the thermistor 4 to the hollow fiber filtration film cartridge 5 through a conduit 2f and a check valve 9 disposed in the middle of the conduit 2f. An acid liquid discharge pipe 2g and an alkaline liquid discharge pipe 2h extend from the non-barrier type electrolytic cell 6. Flow control valves 10a and 10b are disposed in the middle of the acid liquid discharge pipe 2g and the alkaline liquid discharge pipe 2h respectively.

The apparatus 1 further has a control unit 11. The control unit 11 has a DC power circuit including a switching power circuit and a microcomputer programmed to control the switching power circuit. The electric power of the DC power circuit is variable. A flow signal and a temperature signal are input to the control unit 11 from the flow meter 3 and the thermistor 4 respectively. Driving power is supplied to the pump 8 and electrolysis power is supplied to the non-barrier type electrolytic cell 6 from the control unit 11.

The apparatus 1 is connected to a city water faucet through a relief valve 100 for controlling the quantity of supplied water.

The structure of the non-barrier type electrolytic cell 6 will be described.

Figure 2:
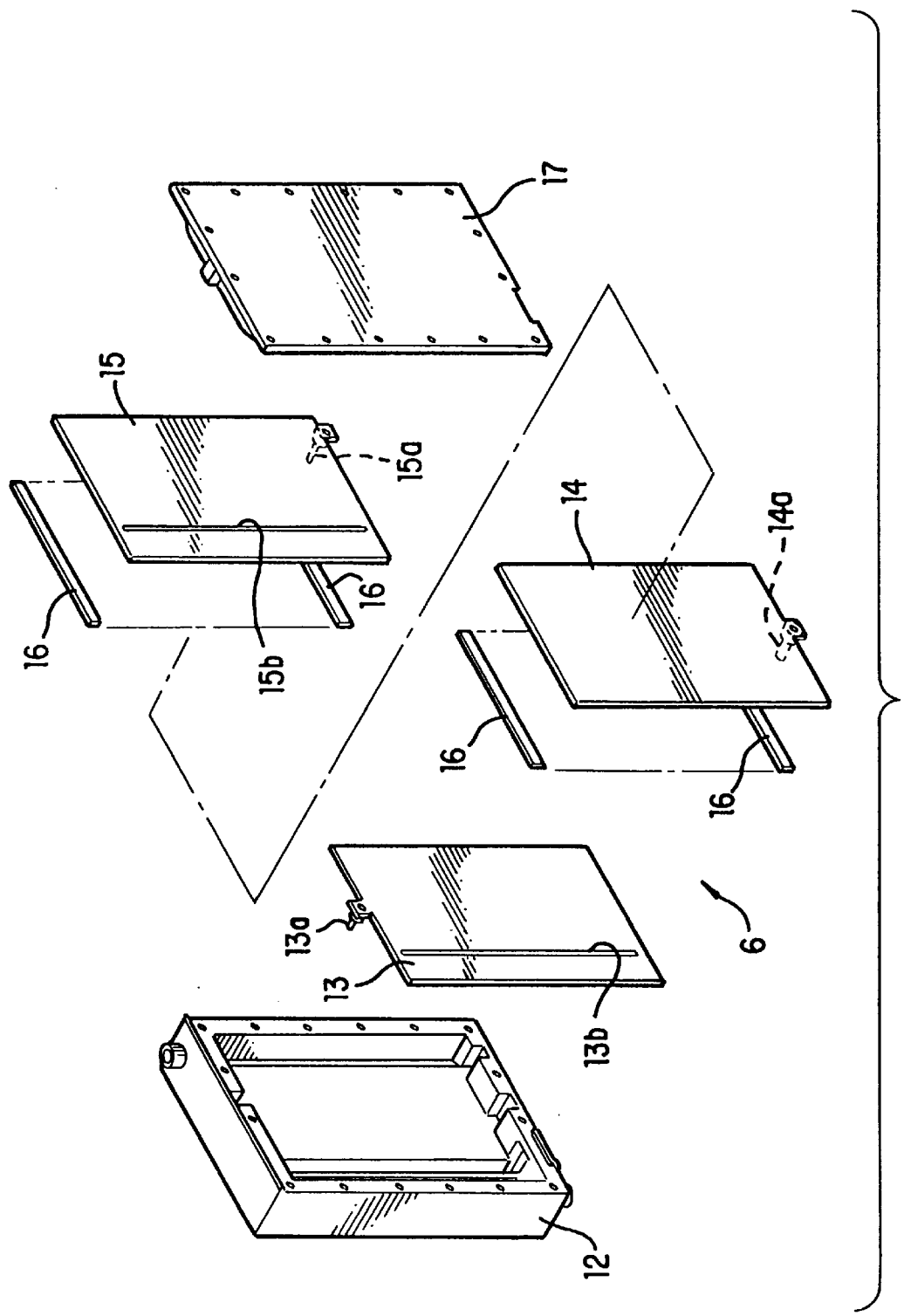
FIG. 2 is an exploded perspective view of a non-barrier type electrolytic cell of an apparatus for generating strong acid sterilizing liquid containing hypochlorous acid at a low concentration in accordance with an embodiment of the present invention.
Figure 3:
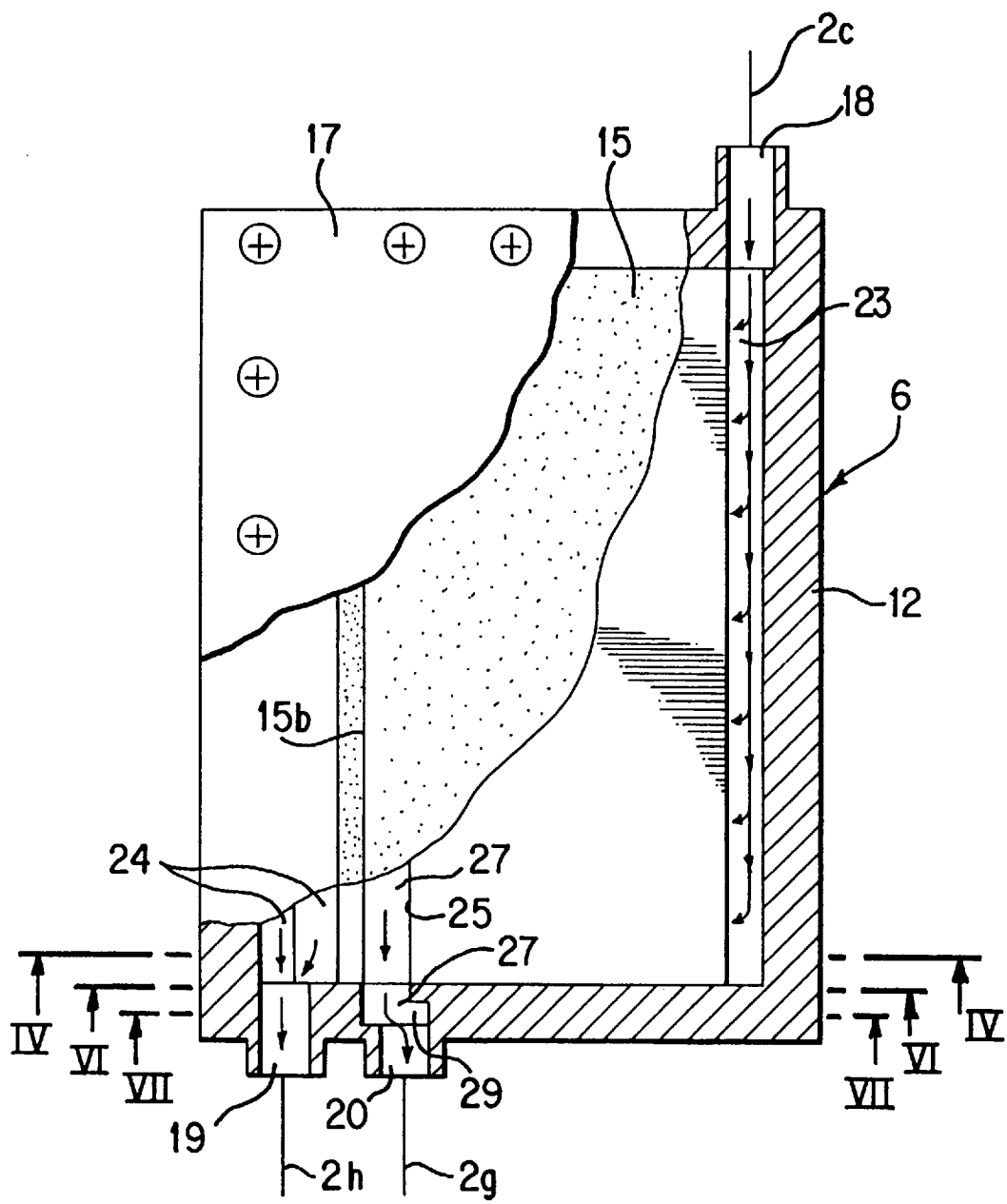
FIG. 3 is a partially cut away back elevation of the electrolytic cell of FIG. 2.

As shown in FIGS. 2 and 3, a rectangular first positive electrode plate 13, a rectangular negative electrode plate 14 and a rectangular second positive electrode plate 15 are set in a concave portion of a pressure case 12 made of resin with plurality of spacers 16 inserted between them. A cover 17 is secured to the case 12 by screws to be watertight. Thus, the non-barrier type electrolytic cell 6 is constituted. The electrode plates 13, 14 and 15 are provided with terminals 13a, 14a and 15a respectively. The terminals 13a, 14a and 15a are connected to the DC power supply of the control unit 11. The case 12 is provided with a salt water inlet port 18, an alkaline liquid outlet port 19 and an acid liquid outlet port 20.

Figure 5:
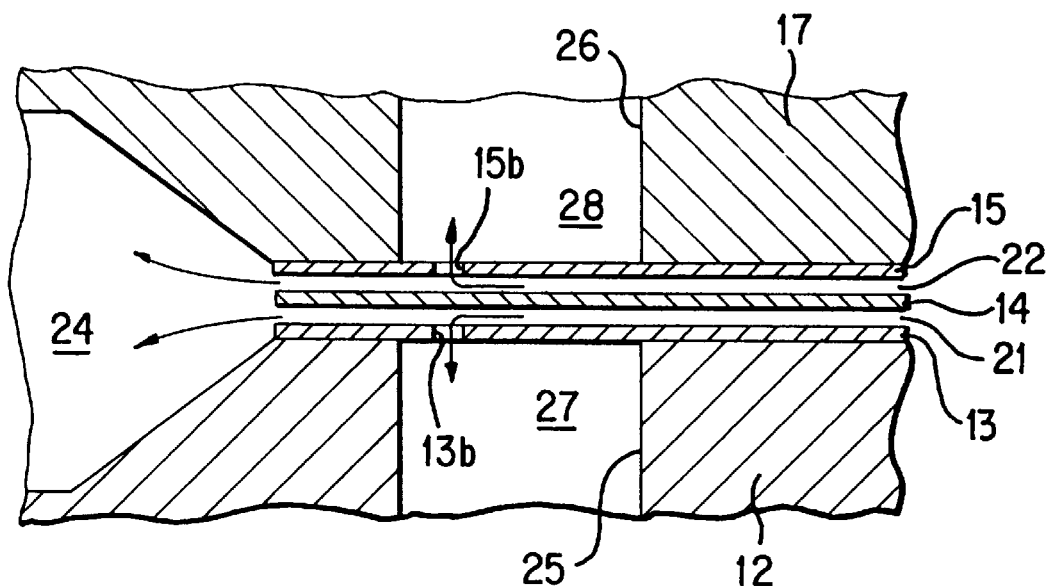
FIG. 5 is an enlarged view of the portion inside the circle A in FIG. 4.

As shown in FIG. 5, a first water flow channel 21 is formed between the first positive electrode plate 13 and the negative electrode plate 14, and a second water flow channel 22 are formed between the negative electrode plate 14 and the second positive electrode plate 15. The spaces between the first positive electrode plate 13 and the negative electrode plate 14, and negative electrode plate 14 and the second positive electrode plate 15 are set sufficiently narrow. The first water flow channel 21 and the second water flow channel 22 are each divided into four horizontal sub-channels by the horizontally extending spacers 16.

Figure 4:
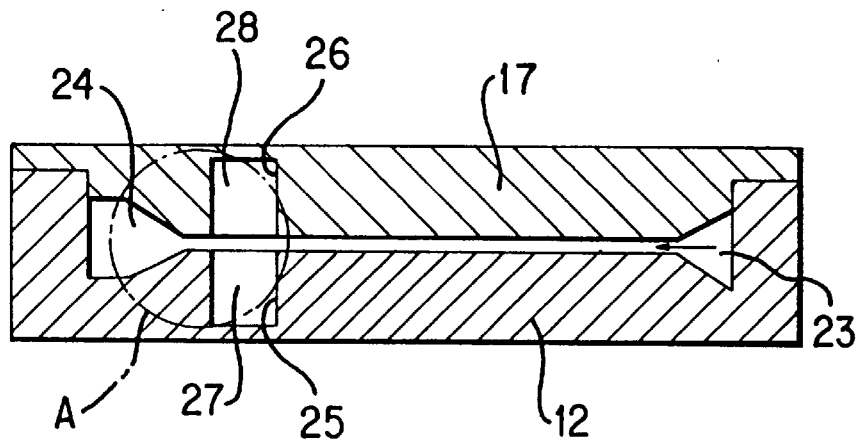
FIG. 4 is a sectional view taken along line IV—IV in FIG. 3 (the electrode plate and the spacer are omitted to simplify of the drawing).

As shown in FIG. 4, the upstream ends of the first water flow channel 21 and the second water flow channel 22 communicate with a salt water distribution channel 23. The salt water distribution channel 23 is constituted by the case 12 and the cover 17 and extends over the whole vertical length of the electrodes. The volume of the salt water distribution channel 23 is large enough relative to the volumes of the first water flow channel 21 and the second water flow channel 22. The shape of the horizontal section of the salt water distribution channel 23 is funnel-like narrowing toward the upstream ends of the first water flow channel 21 and the second water flow channel 22 so as to increase the structural continuity in the region where the salt water distribution channel 23 communicates with the first water flow channel 21 and the second water flow channel 22. As shown in FIG. 3, the upstream end of the salt water distribution channel 23 communicates with the salt water inlet port 18. The salt water inlet port 18 is connected to the conduit 2c.

Figure 6:
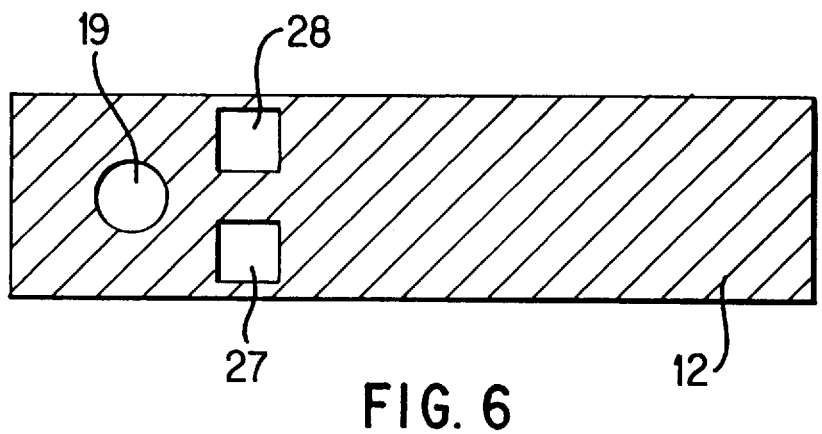
FIG. 6 is a sectional view taken along line VI—VI in FIG. 3.
Figure 7:
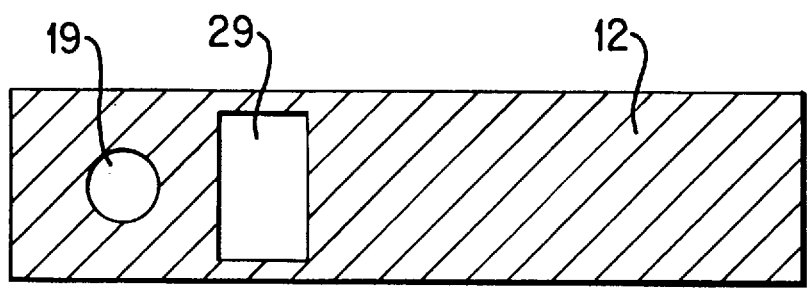
FIG. 7 is a sectional view taken along line VII—VII in FIG. 3.

As shown in FIGS. 4 and 5, the downstream ends of the first water flow channel 21 and the second water flow channel 22 communicate with an alkaline liquid recovery channel 24. The alkaline liquid recovery channel 24 is constituted by the case 12 and the cover 17 and extends over the whole vertical length of the electrodes. The volume of the alkaline liquid recovery channel 24 is large enough relative to the volumes of the first water flow channel 21 and the second water flow channel 22. As shown in FIGS. 3, 6 and 7, the downstream end of the alkaline liquid recovery channel 24 communicates with the alkaline liquid outlet port 19. The alkaline liquid outlet port 19 is connected to the alkaline liquid discharge pipe 2h.

As shown in FIGS. 4 and 5, the case 12 is provided with a groove 25 extending over the whole vertical length of the first positive electrode 13. The cover 17 is provided with a groove 26 extending over the whole vertical length of the second positive electrode 15. The groove 25 forms a first acid liquid recovery channel 27 in collaboration with the first positive electrode 13. The groove 26 forms a second acid liquid recovery channel 28 in collaboration with the second positive electrode 15. As shown in FIG. 3, 6 and 7, the downstream portions of the first acid liquid recovery channel 27 and the second acid liquid recovery channel 28 extend into the case 12 and the downstream ends of the first acid liquid recovery channel 27 and the second acid liquid recovery channel 28 communicate with a connection port 29 formed in the case 12. The connection port 29 communicates with the acid liquid outlet port 20. The acid liquid outlet port 20 is connected to the acid liquid discharge pipe 2g.

As shown in FIGS. 2 and 5, the first positive electrode 13 is provided with a vertically extending slit 13b at the downstream portion of the first water flow channel 21. The first water flow channel 21 communicates with the first acid liquid recovery channel 27 through the slit 13b. As shown in FIGS. 2, 3 and 5, the second positive electrode 15 is provided with a vertically extending slit 15b at the downstream portion of the second water flow channel 22. The second water flow channel 22 communicates with the second acid liquid recovery channel 28 through the slit 15b.

The apparatus 1 for generating strong acid sterilizing liquid containing hypochlorous acid at a low concentration operates as follows.

As indicated by hollow arrows in FIG. 1, city water is discharged from the water faucet. The flow rate of the city water is controlled by the relief valve 100. The city water flows into the hollow fiber filtration film cartridge 5 through the flow meter 3 and the thermistor 4. The flow rate of the city water is detected by the flow meter 3 and the temperature of the city water is detected by the thermistor 4. The flow meter 3 sends a flow rate signal to the control unit 11 and the thermistor 4 sends a temperature signal to the control unit 11.

When the temperature of the city water is higher than a prescribed value, a control signal is sent to a display (not shown in Figures), and an alarm is displayed to warn the user to close the faucet and stop the water flow so as to prevent damage to the hollow fiber filtration films.

Highly concentrated salt water stored in the salt water tank 7 is fed to the conduit 2b through the pump 8 and is diluted by mixing with the city water flowing in the conduit 2*b*. The diluted salt water passes into the hollow fiber filtration film cartridge 5. The driving power of the pump 8 is controlled by the control unit 11 based on the flow rate of the city water detected by the flow meter 3, i.e., the flow rate of the city water in the conduit 2*b*, so as to control the quantity of the highly concentrated salt water fed to the conduit 2*b* and the salt concentration of the salt water passing into the hollow fiber filtration film cartridge 5. The check valve 9 prevents the city water from flowing into the salt water tank 7 from the conduit 2*b*.

The salt water passed into the hollow fiber filtration film cartridge 5 is filtered by the hollow fiber filtration films charged in the cartridge 5. Thus, bacteria and other contaminant are removed from the salt water. The salt water free from bacteria and other contaminants passes into the non-barrier type electrolytic cell 6.

As indicated by arrows in FIGS. 3 and 4, the salt water passed into the salt water inlet port 18 of the non-barrier type electrolytic cell 6 passes into the salt water distribution channel 23. The salt water flows down the salt water distribution channel 23 and horizontally into the four subchannels of each of the first water flow channel 21 and the second water flow channel 22.

The DC power unit of the control unit 11 applies DC voltage across the negative electrode plate 14 and the first and the second positive electrode plates 13 and 15. The salt water flowing horizontally in the first water flow channel 21 and the second water flow channel 22 is electrolyzed. Acid liquid containing hypochlorous acid is generated near the first positive electrode plate 13 and the second positive electrode plate 15, and alkaline liquid is generated near the negative electrode plate 14. The control unit 11 controls the electric power for the electrolysis so as to control the pH and the hypochlorous acid concentration of the acid liquid.

As shown in FIG. 5, the acid liquid containing hypochlorous acid generated near the first positive electrode plate 13 and flowing along the first positive electrode plate 13 passes into the first acid liquid recovery channel 27 from the downstream portion of the first water flow channel 21 through the slit 13*b* formed in the first positive electrode plate 13. The acid liquid containing hypochlorous acid generated near the second positive electrode plate 15 and flowing along the second positive electrode plate 15 passes into the second acid liquid recovery channel 28 from the downstream portion of the second water flow channel 22 through the slit 15*b* formed in the second positive electrode plate 15. As shown in FIG. 3, the acid liquid containing hypochlorous acid passed into the first acid liquid recovery channel 27 and the second acid liquid recovery channel 28 flows down into the connection port 29 and flows out of the non-barrier type electrolysis cell 6 through the acid liquid outlet port 20.

As shown in FIG. 5, the alkaline liquid generated near the negative electrode plate 14 and flowing along the negative electrode plate 14 passes into the alkaline liquid recovery channel 24 from the downstream ends of the first water flow channel 21 and the second water flow channel 22. As shown in FIG. 3, the alkaline liquid passed into the alkaline liquid recovery channel 24 flows down and flows out of the non-barrier type electrolysis cell 6 through the alkaline liquid outlet port 19.

In the non-barrier type electrolysis cell 6, each of the positive electrode plates 13 and 15 is disposed opposite the negative electrode plate 14 without a barrier between them. Thus, the space between the electrodes can be made narrower than that in the conventional barrier type electrolytic cell so as to increase the flow speed of the salt water in the first water flow channel 21 and the second water flow channel 22 formed between the electrodes, and thereby increase the number of hydroxide ions and hydrogen ions supplied to the surfaces of the electrodes. Thus, strong acid electrolyzed water can be obtained without increasing the voltage applied across the electrodes, while suppressing the generation of hypochlorous acid.

In the non-barrier type electrolysis cell 6, the distances between the electrodes are sufficiently small, the volume of the salt water distribution channel 23 is large enough relative to the volumes of the first water flow channel 21 and the second water flow channel 22, and the shape of the horizontal section of the salt water distribution channel 23 is funnel-like, narrowing toward the upstream ends of the first water flow channel 21 and the second water flow channel 22. Thus, the salt water passed into the first water flow channel 21 and the second water flow channel 22 immediately forms a laminar flow. Thus, the layers of the flow of the strong acid electrolyzed water passing along the first positive electrode 13 and the second positive electrode 15 do not mix with the layers of the flow of the strong alkaline electrolyzed water passing along the negative electrode 14.

In the non-barrier type electrolysis cell 6, the layer of the flow of the strong acid electrolyzed water passing along the first positive electrode plate 13 is taken out from the downstream portion of the first water flow channel through the slit 13*b* formed in the first positive electrode plate 13, and the layer of the flow of the strong acid electrolyzed water passing along the second positive electrode plate 15 is taken out from the downstream portion of the second water flow channel through the slit 15*b* formed in the second positive electrode plate 15. Thus, strong acid electrolyzed water containing hypochlorous acid at a low concentration can be obtained.

The strong acid electrolyzed water containing hypochlorous acid at a low concentration flowing out of the non-barrier type electrolytic cell 6 through the acid liquid outlet port 20 discharges the apparatus 1 through the flow rate control valve 10*a*. The alkaline liquid flowing out of the non-barrier type electrolytic cell 6 through the alkaline liquid outlet port 19 discharges form the apparatus 1 through the flow rate control valve 10*b*. The ratio of the flow rate of the acid liquid discharging from the apparatus 1 to the alkaline liquid discharging from the apparatus 1 can be controlled by the flow rate control valves 10*a* and 10*b*.

2. Tests of Disposition of Strong Acid Electrolyzed Water Containing Hypochlorous Acid at a Low Concentration.

Tests of generation of strong acid electrolyzed water containing hypochlorous acid at a low concentration were carried out using the apparatus 1 and varying the concentration of the salt in the salt water supplied to the non-barrier type electrolytic cell.

a. Test conditions size of the electrodes: breadth (excluding the parts in contact with the spacers)×length: 100 mm×60 mm material of the electrodes: JIS 2 class pure titanium+ platinum galvanizing distance between the electrodes: 0.5 mm electric power for electrolysis: 30 W flow rate: total flow rate: 2 liter/minute (acid liquid, alkaline liquid: each 1 liter/minute)

city water: pH: 7, residual chlorine concentration: 0.1 ppm or less, temperature: 25° C.

method for detecting the concentration of hypochlorous acid: DPD (diethyl-p-phenylendiamine) method b. Test results The test results are shown in FIGS. 8 and 9.

Figure 8:
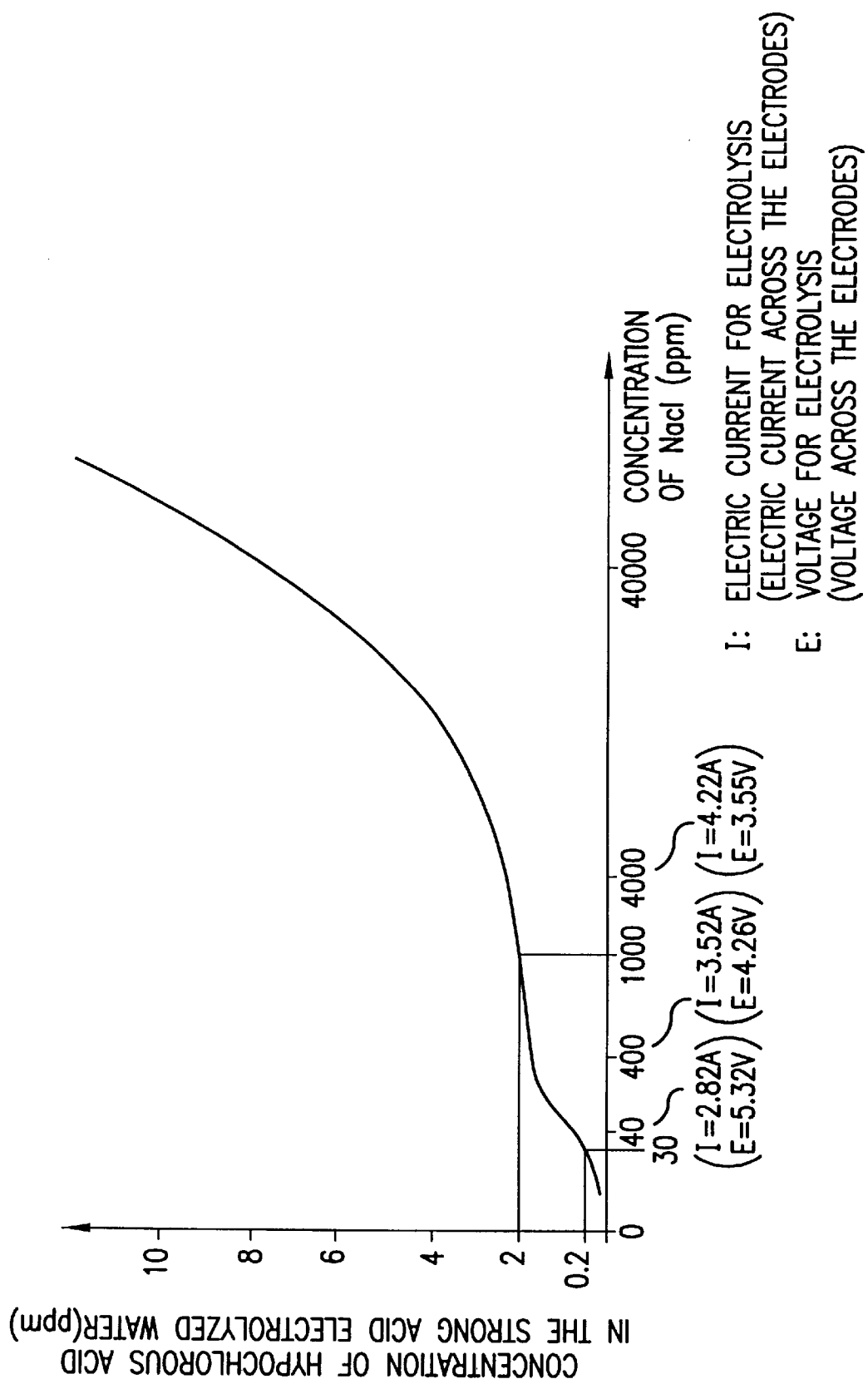
FIG. 8 is a graph showing the results of generation tests of strong acid sterilizing liquid containing hypochlorous acid at a low concentration, which were carried out using an apparatus for generating strong acid sterilizing liquid containing hypochlorous acid at a low concentration in accordance with an embodiment of the present invention.
Figure 9:
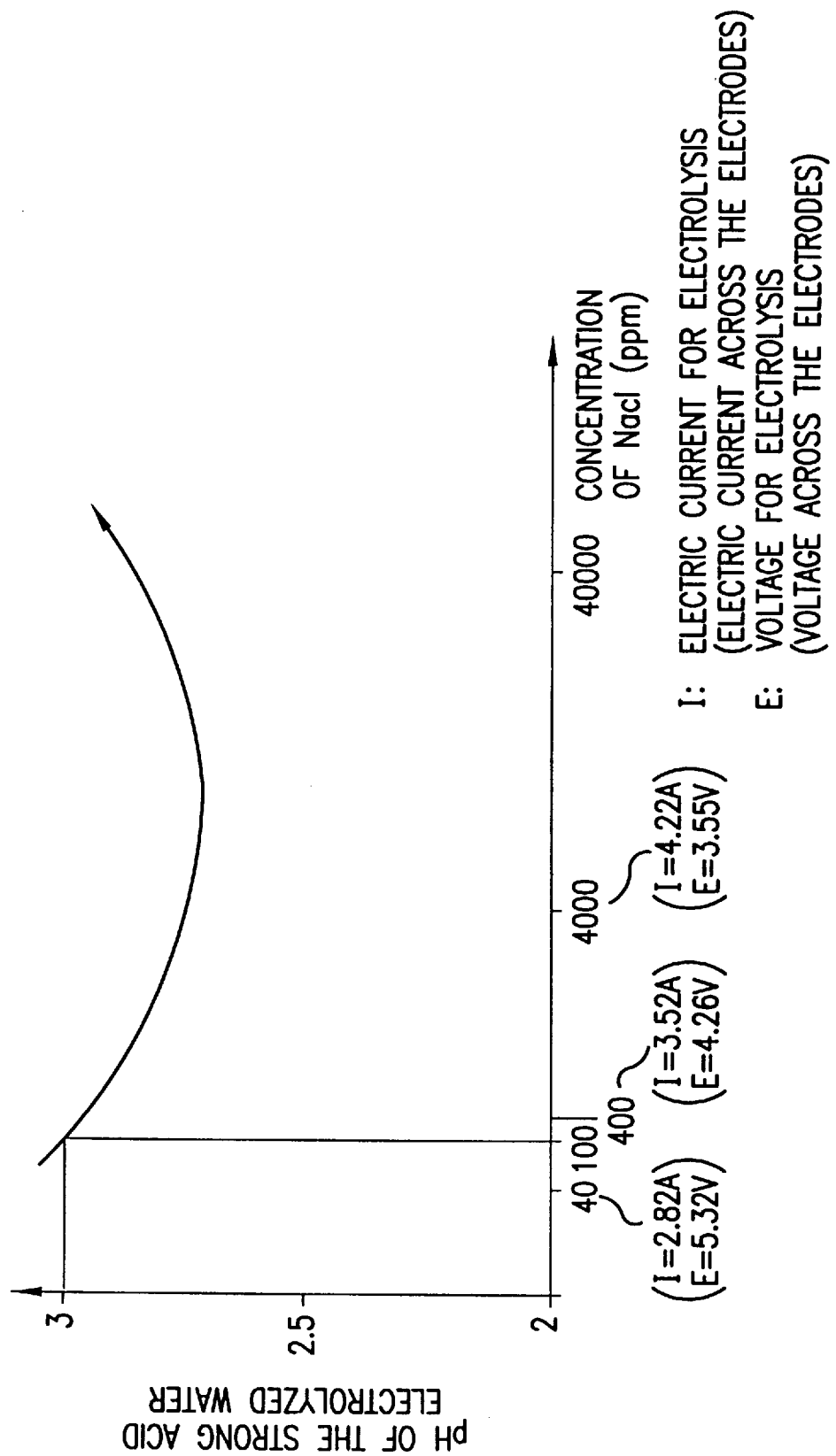
FIG. 9 is a graph showing the results of another generation tests of strong acid sterilizing liquid containing hypochlorous acid at a low concentration, which were carried out using an apparatus for generating strong acid sterilizing liquid containing hypochlorous acid at a low concentration in accordance with an embodiment of the present invention.

As seen from FIGS. 8 and 9, in the present tests, strong acid electrolyzed water whose pH was 3 or less and wherein the concentration of hypochlorous acid was 2 ppm or less was obtained when the concentration of salt in the salt water supplied to the non-barrier type electrolytic cell 6 was 100 ppm to 1000 ppm. Thus, it was confirmed that strong acid electrolyzed water whose pH is 3 or less and wherein the concentration of hypochlorous acid is 2 ppm or less can be obtained by the use of the apparatus 1 for generating the strong acid sterilizing liquid containing hypochlorous acid at a low concentration. It is thought that the concentration of salt in the salt water which enables the generation of the strong acid electrolyzed water whose pH is 3 or less and wherein the concentration of hypochlorous acid is 2 ppm or less varies with the distance between the electrodes, flow rate of the salt water, etc.

3. Test Confirming the Bactericidal Activity of Strong Acid Electrolyzed Water Containing Hypochlorous Acid at a Low Concentration.

a. Tests Confirming the Bactericidal Activity against *Escherichia coli*.

Tests confirming the bactericidal activity against *Escherichia coli* (*Escherichia coli* IFO15034) were carried out on four kinds of strong acid electrolyzed water containing hypochlorous acid at a low concentration whose pH was about 2.5 and wherein the concentration of hypochlorous acid was 0.10 ppm to 11.8 ppm generated by the use of the apparatus 1 for generating strong acid sterilizing liquid containing hypochlorous acid at a low concentration, and distilled water wherein the concentration of hypochlorous acid was 0.02 ppm. Test conditions are shown in Table 1.

Figure 10:
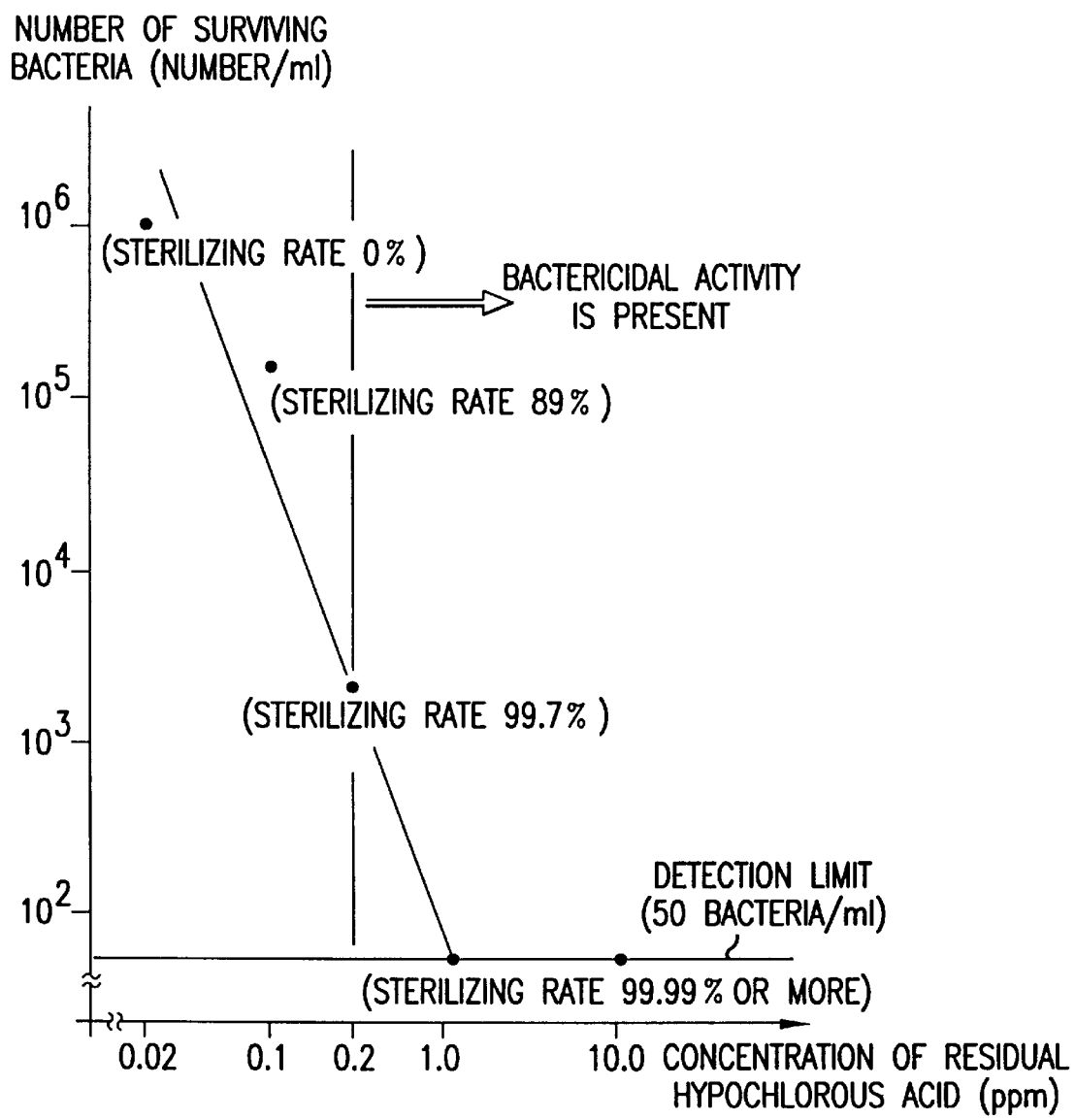
FIG. 10 is a graph showing the results of bactericidal activity confirmation tests of strong acid sterilizing liquid containing hypochlorous acid generated by an apparatus for generating strong acid sterilizing liquid containing hypochlorous acid at a low concentration in accordance with an embodiment of the present invention.

Test results are shown in Table 2 and FIG. 10.

From Table 2 and FIG. 10, it can be seen that strong acid electrolyzed water containing hypochlorous acid whose pH was 3 or less and wherein the concentration of hypochlorous acid was 0.2 ppm or more generated by the use of the apparatus 1 for generating strong acid sterilizing liquid containing hypochlorous acid at a low concentration could substantially achieve a sterilizing rate of 99.9%, which is considered to be the criterion of the presence of bactericidal activity. The sterilizing rate referred to here is expressed as follows. The sterilizing rate (%)=(1−number of surviving bacteria/number of tested bacteria)×100.

b. Tests Confirming the Bactericidal Activity against Various Kinds of Bacteria.

Confirmation tests of the bactericidal activity against *Escherichia coli* (*Escherichia coli* ATCC 8739), *Staphylococcus aureus* (*Staphylococcus aureus* ATCC 6538P), *Streptococcus pyogenes* (*Streptococcus pyogenes* HIC 2101), *Pseudomonas aeruginosa* (*Pseudomonas aeruginosa* HIC 1803), MRSA (*Staphylococcus aureus*(MRSA) HIC 2011), *Salmonella typhimurium* (*Salmonella typhimurium* ATCC 13311), *Bacillus subtilis* (*Bacillus subtilis* ATCC 11778) were carried out on strong acid electrolyzed water containing hypochlorous acid at a low concentration whose pH was 2.42 and wherein the concentration of hypochlorous acid was 0.54 ppm and strong acid electrolyzed water containing hypochlorous acid at a low concentration whose pH was 2.42 and wherein the concentration of hypochlorous acid was 2.34 ppm generated by the use of the apparatus 1 for generating strong acid sterilizing liquid containing hypochlorous acid at a low concentration.

(i) Test Conditions.

Adjusting of the liquid containing bacteria: same as Table 1

Medium for counting the number of bacteria: same as Table 1

Testing method: liquid containing bacteria was diluted to 1/10 .to 1/100, 0.1 ml of the diluted liquid was poured in 10 ml of the sterilizing liquid, and the the diluted liquid was contacted with the sterilizing liquid for a prescribed length of time ranging 5 to 300 seconds. After the passage of the prescribed time, the tested liquid was neutralized by addition of aqueous solution of sodium thiosulfate.

The neutralized tested liquid was stepwise diluted by adding physiological salt water. The number of surviving bacteria was counted by the smear method (35° C., 48 hours of culture).

(ii) Test Results

The test results of the strong acid electrolyzed water containing hypochlorous acid at a low concentration whose pH was 2.42 and wherein the concentration of hypochlorous acid was 0.54 ppm is shown in Table 3. Test results of the strong acid electrolyzed water containing hypochlorous acid at a low concentration whose pH was 2.42 and wherein the concentration of hypochlorous acid was 2.34 ppm is shown in Table 4.

From Table 3, it can be seen that strong acid electrolyzed water containing hypochlorous acid whose pH was 2.42 and wherein the concentration of hypochlorous acid was 0.54 ppm generated by the use of the apparatus 1 had bactericidal activity against *Escherichia coli, Staphylococcus aureus, Streptococcus pyogenes, Pseudomonas aeruginosa*, MRSA, and *Salmonella typhimurium*. From Table 4, it can be seen that strong acid electrolyzed water containing hypochlorous acid whose pH was 2.42 and wherein the concentration of hypochlorous acid was 2.34 ppm generated by the use of the apparatus 1 had bactericidal activity against the above mentioned bacteria and also *Bacillus subtilis*.

From the above mentioned confirmation tests (i) and (ii), it was confirmed that strong acid electrolyzed water whose pH was 3 or less and wherein the concentration of hypochlorous acid was 2 ppm or less generated by the use of the apparatus 1 for generating strong acid sterilizing liquid containing hypochlorous acid at a low concentration had sufficient bactericidal activity.

c. Correlation Tests between pH, Concentration of Hypochlorous Acid and the Bactericidal Activity of the Strong Acid Sterilizing Liquid Containing Hypochlorous Acid at a Low Concentration.

Confirmation tests of the bactericidal activity against *Escherichia coli* (*Escherichia coli* IFO15034) and *Staphylococcus aureus* (*Staphylococcus aureus* IFO13276) were carried out on strong acid electrolyzed water containing hypochlorous acid at a low concentration whose pH was 2.3 to 7.0 and wherein the concentration of hypochlorous acid was 0.5 ppm to 2.0 ppm generated by the use of the apparatus 1 for generating strong acid sterilizing liquid containing hypochlorous acid at a low concentration. Based on the test results, correlations between pH, concentration of hypochlorous acid and the bactericidal activity of the strong acid sterilizing liquid containing hypochlorous acid at a low concentration were obtained.

(i) Test Conditions adjusting of the liquid containing bacteria: same as Table 1 medium for counting the number of bacteria: same as Table 1 testing method: same as Table 1 except that the time of contact of the liquid containing the bacteria contacts with the sterilizing liquid was set at 5 seconds.

(ii) Test Results

The results of the bactericidal activity confirmation tests against *Escherichia coli* are shown in Table 5.

The results of the bactericidal activity confirmation tests against Staphylococcus aureus are shown in Table 6.

From Table 5, it can be seen that strong acid electrolyzed water containing hypochlorous acid wherein the concentration of hypochlorous acid was 0.5 ppm or more could sterilize Escherichia coli irrespective of the pH of the liquid.

From Table 6, it can be seen that strong acid electrolyzed water containing hypochlorous acid whose pH was 3.0 or less could sterilize Staphylococcus aureus even when the concentration of hypochlorous acid was 0.5 ppm and that strong acid electrolyzed water containing hypochlorous acid wherein the concentration of hypochlorous acid was 1.5 ppm or more could sterilize Staphylococcus aureus irrespective of the pH of the liquid.

4. An Apparatus for Generating and Spraying Strong Acid Sterilizing Liquid Containing Hypochlorous Acid at a Low Concentration.

Figure 13:
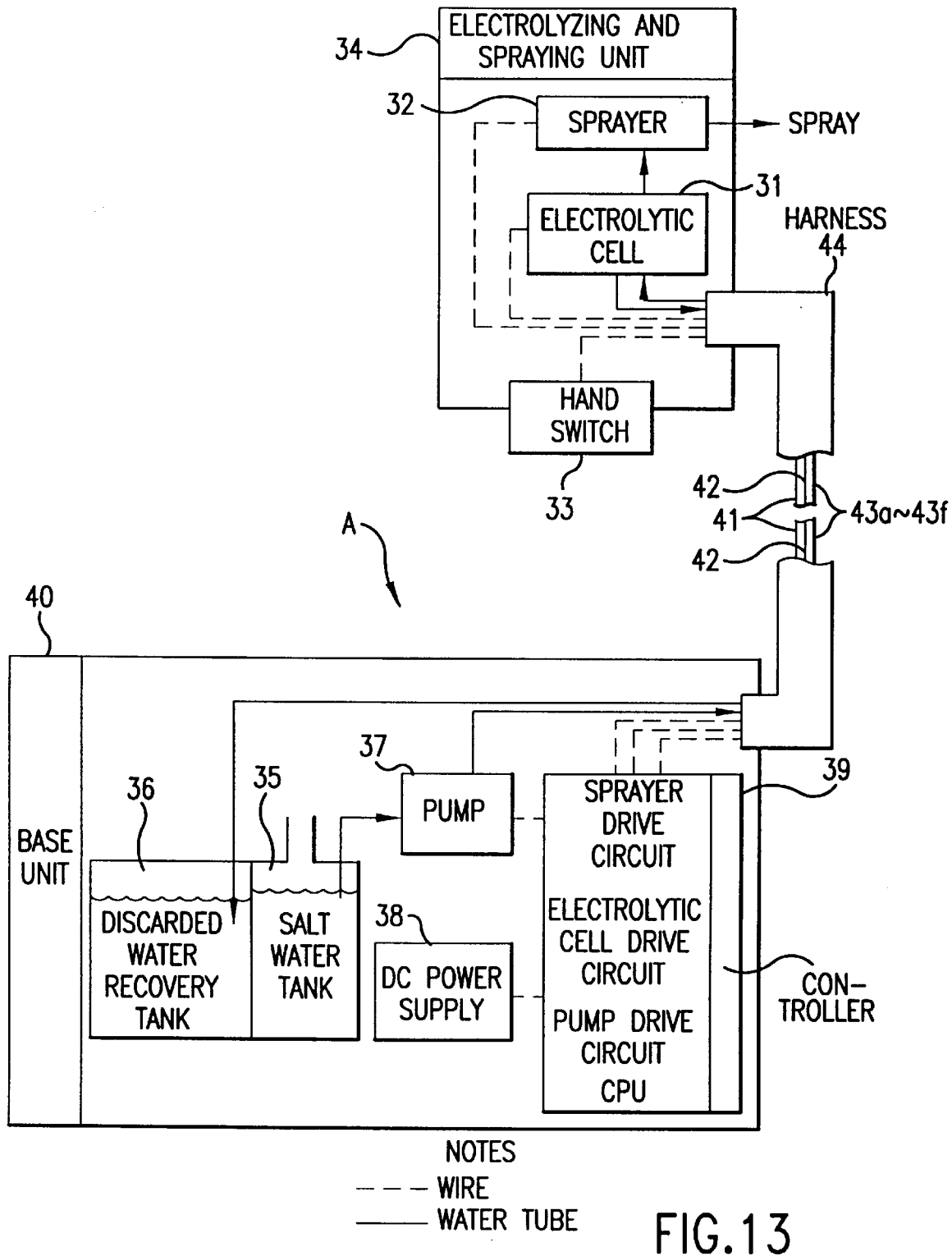
FIG. 13 is a layout of an apparatus for generating and spraying strong acid sterilizing liquid containing hypochlorous acid at a low concentration in accordance with an embodiment of the present invention.

As shown in FIG. 13, an apparatus A for generating and spraying strong acid sterilizing liquid containing hypochlorous acid at a low concentration in accordance with an embodiment of the present invention has a palm sized electrolyzing and spraying unit 34 including a non-barrier type electrolytic cell 31, a sprayer 32 and a hand switch 33, a base unit 40 including a salt water tank 35, a discarded water recovery tank 36, a pump 37, a DC power supply 38 provided with a dry battery or a rechargeable battery and a controller 39, and a harness 44 including a salt water supply tube 41, a discarded water discharge tube 42, wires 43a, 43b for electrolysis, wires 43c, 43d for a piezoelectric element and wires 43e, 43f for the hand switch. The harness 44 connects the base unit 40 to the electrolyzing and spraying unit 34.

The controller 39 has a sprayer drive circuit provided with a constant voltage circuit and a high frequency generation circuit, an electrolytic cell drive circuit provided with a constant current circuit, a pump drive circuit provided with a constant voltage circuit, and a CPU.

Figure 14:
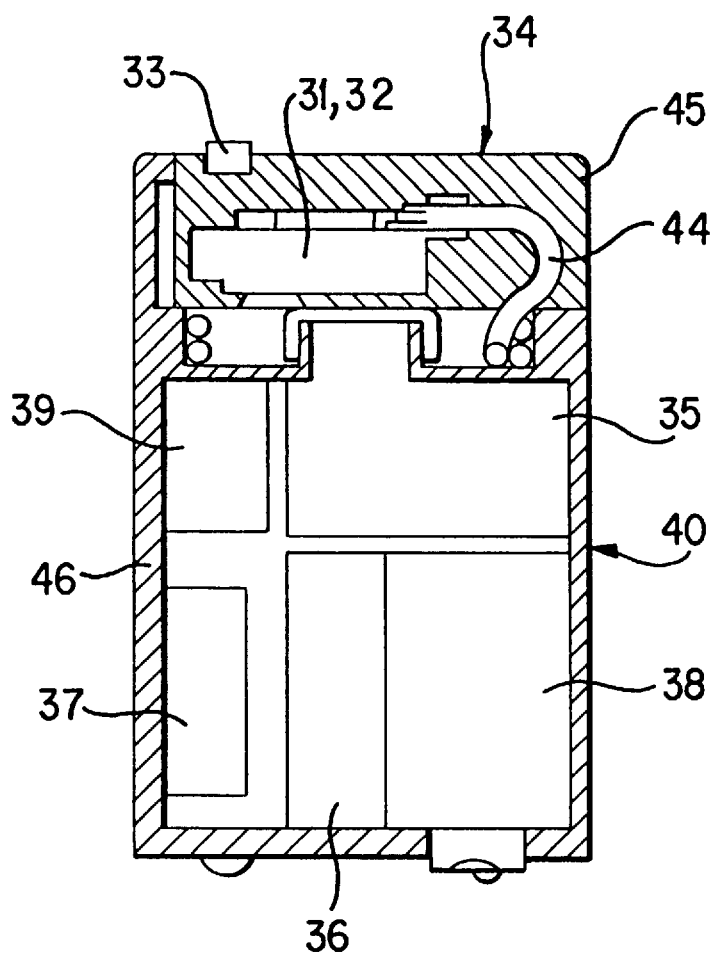
FIG. 14 is a sectional view of an apparatus for generating and spraying strong acid sterilizing liquid containing hypochlorous acid at a low concentration in accordance with an embodiment of the present invention, showing the general structure of the apparatus.
Figure 15C:
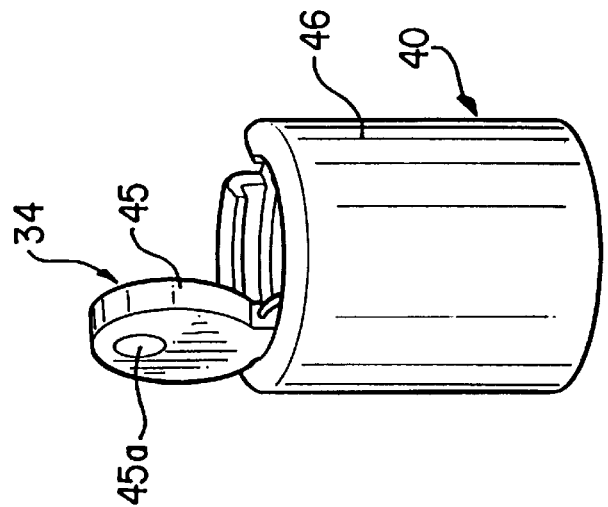
FIG. 15($a$) is a perspective view of an apparatus for generating and spraying strong acid sterilizing liquid containing hypochlorous acid at a low concentration in accordance with an embodiment of the present invention, showing the electrolyzing and spraying unit accommodated in a base unit, FIG. 15($b$) is a perspective view of an apparatus for generating and spraying strong acid sterilizing liquid containing hypochlorous acid at a low concentration in accordance with an embodiment of the present invention, showing the electrolyzing and spraying unit taken out of the base unit, and FIG. 15($c$) is a perspective view of an apparatus for generating and spraying strong acid sterilizing liquid containing hypochlorous acid at a low concentration in accordance with an embodiment of the present invention, showing the electrolyzing and spraying unit hooked on the base unit.
Figure 15B:
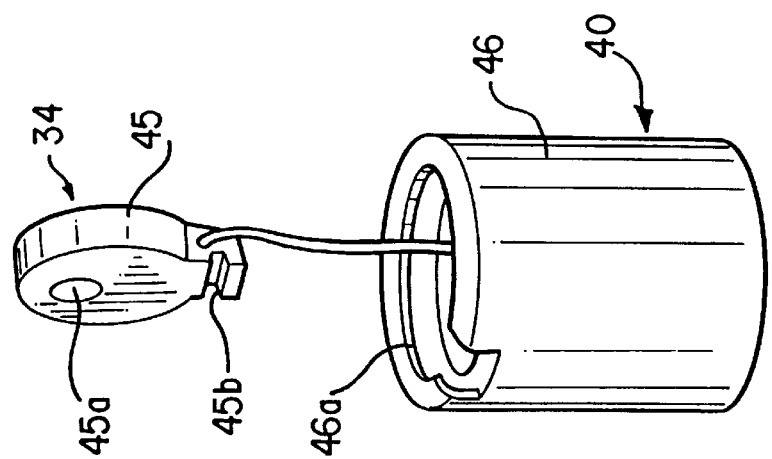
Figure 15A:
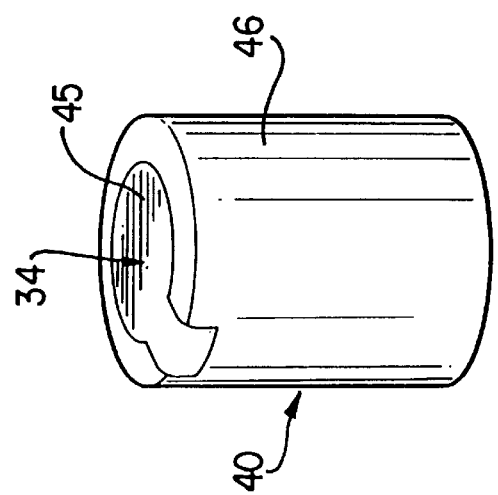

As shown in FIGS. 14 and 15(a) to 15(c), the non-barrier type electrolytic cell 31, the sprayer 32 and the hand switch 33 of the electrolyzing and spraying unit 34 are housed in a thick disk case 45 whose diameter×thickness is about 90 mm×about 35 mm. The case 45 is provided with an acid mist supply opening 45a. The salt water tank 35, the discarded water recovery tank 36, the pump 37, the DC power supply 38 provided with a dry battery or a rechargeable battery and the controller 39 of the base unit 40 are housed in a cylindrical case 46 provided with a bottom plate and whose diameter×depth is about 105 mm×about 180 mm. As shown in FIGS. 14, 15(a) and 15(b), the electrolyzing and spraying unit 34 and the harness 44 can be accommodated in the recess of the base unit 40 and taken out from the recess of the base unit 40. As shown in FIGS. 15(b) and 15(c), a groove 45b formed in the case 45 can be engaged with a flange 46a formed around the recess of the case 46 to hook the electrolyzing and spraying unit 34 upright on the base unit 40.

Figure 16A:
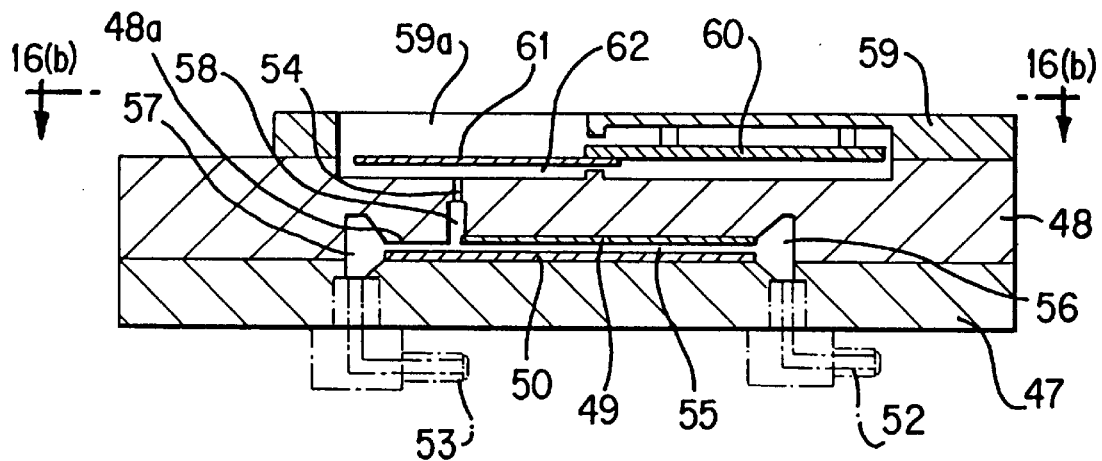
FIG. 16($a$) is a sectional view of the electrolyzing and spraying unit of an apparatus for generating and spraying strong acid sterilizing liquid containing hypochlorous acid at a low concentration in accordance with an embodiment of the present invention, and FIG. 16($b$) is a sectional view taken along line b—b in FIG. 16($a$).
Figure 17:
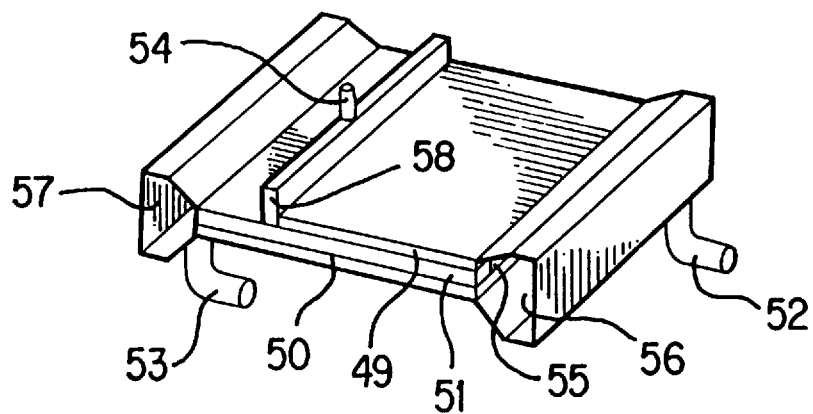
FIG. 17 is a perspective view of the electrolytic cell of the electrolyzing and spraying unit of FIG. 16($a$) and FIG. 16($b$).
Figure 18:
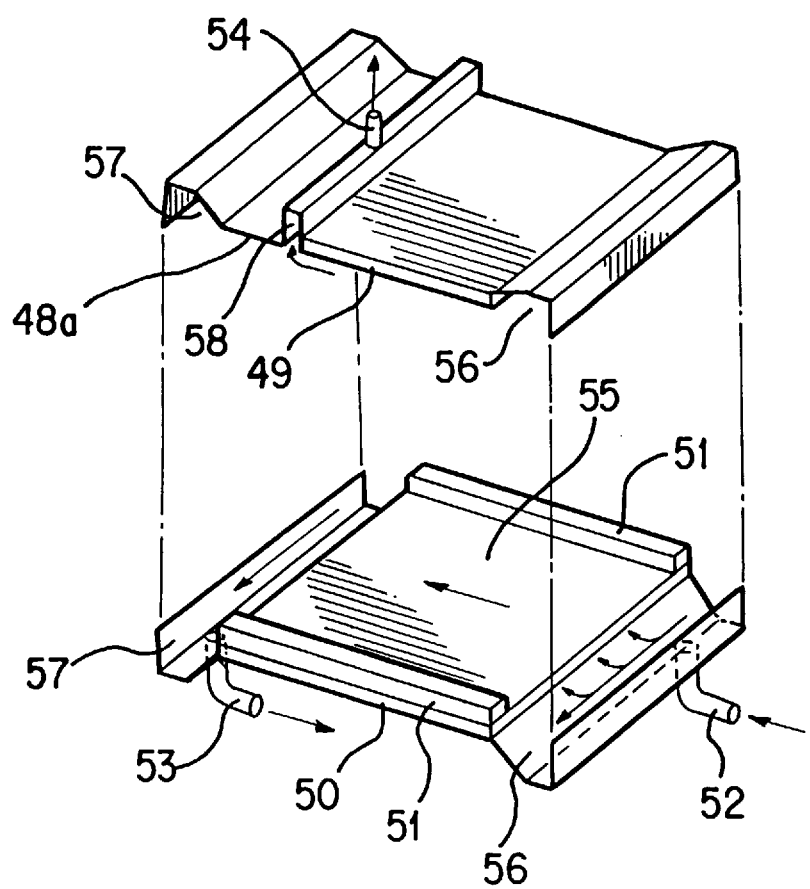
FIG. 18 is a perspective view of the electrolytic cell of the electrolyzing and spraying unit of FIG. 16($a$) and FIG. 16($b$), showing the electrolytic cell divided into the positive electrode side part and the negative electrode side part.

As shown in FIGS. 16(a), 17 and 18, a concave resin pressure case 47 whose length×width×depth is about 60 mm×about 50 mm×about 5 mm and a concave resin pressure cover 48 whose length×width×depth is about 60 mm×about 50 mm×about 7 mm are screwed to each other to be watertight. A positive electrode plate 49, a negative electrode plate 50 and a pair of resin spacers 51 disposed between the electrode plates are held in a recess between the case 47 and the cover 48. Thus, the non-barrier type electrolytic cell 31 is constituted.

The positive electrode plate 49 is constituted of a titanium plate coated with platinum. The length×width of the positive electrode plate 49 is about 20 mm×about 16 mm (excluding the part in contact with the spacers 51). The negative electrode plate 50 is constituted of a titanium plate coated with platinum. The length×width of the negative electrode plate 50 is about 25 mm×about 16 mm (excluding the part in contact with the spacers 51). The size of the electrode plates 49, 50 are determined considering the quantity of water to be electrolyzed per unit time which is decided based on the quantity of mist to be sprayed per unit time determined considering the fact that the sterilizing liquid is sprayed on diseased parts of a rather small area, the quantity of electric current per unit quantity of water to be electrolyzed necessary for generating strong acid liquid whose pH is 3 or less, and the upper limit of the electric current to which the required suppression of chlorine generation can be achieved. The electrode plates 49, 50 are connected to the electrolytic cell drive circuit of the controller 39 through terminals which are not shown and the wires 43a, 43b of the harness 44.

The case 47 is provided with a salt water inlet port 52 and an alkaline liquid outlet port 53. The cover 48 is provided with an acid liquid outlet port 54.

A water flow channel 55 is formed between the positive electrode plate 49 and the negative electrode plate 50. The downstream end portion of the water flow channel 55 is constituted by a flat surface 48a of the cover 48 which is formed in the concave portion of the cover 48 and extends flush with the positive electrode plate 49 and the negative electrode plate 50. The space between the positive electrode plate 49 and the negative electrode plate 50 is set at about 0.2 mm to 0.5 mm. The space between the electrode plates is determined considering the optimum flow resistance determined from the quantity of water to be electrolyzed per unit time and the output of the pump 37 driven by the battery, the lowering of the voltage applied across the electrodes necessary for achieving the electrolysis driven by the battery, and decrease of the quantity of the residual water in the non-barrier type electrolytic cell necessary for achieving the reduction of the quantity of the sprayed liquid at the start of the spraying operation.

The upstream end of the water flow channel 55 communicates with a salt water supply channel 56. The salt water supply channel 56 is constituted by the case 47 and the cover 48. The salt water supply channel 56 extends over the whole width of the electrode plates. The salt water supply channel 56 communicates with the salt water inlet port 52. The salt water inlet port 52 communicates with the salt water tank 35 of the base unit 40 through the salt water supply tube 41 of the harness 44 and the pump 37 of the base unit 40.

The downstream end of the water flow channel 55 communicates with an alkaline liquid recovery channel 57. The alkaline liquid recovery channel 57 is constituted by the case 47 and the cover 48. The alkaline liquid recovery channel 57 extends over the whole width of the electrode plates. The volume of the alkaline liquid recovery channel 57 is large enough relative to the volume of the water flow channel 55.

The downstream end of the alkaline liquid recovery channel 57 communicates with the alkaline liquid outlet port 53. The alkaline liquid outlet port 53 communicates with the discarded water recovery tank 36 of the base unit 40 through the discarded water discharge tube 42 of the harness 44.

The cover 48 is provided with an acid liquid recovery channel 58 extending adjacent to the downstream end of and over the whole width of the positive electrode plate 49. The acid liquid recovery channel 58 communicates with the acid liquid outlet port 54.

Figure 16B:
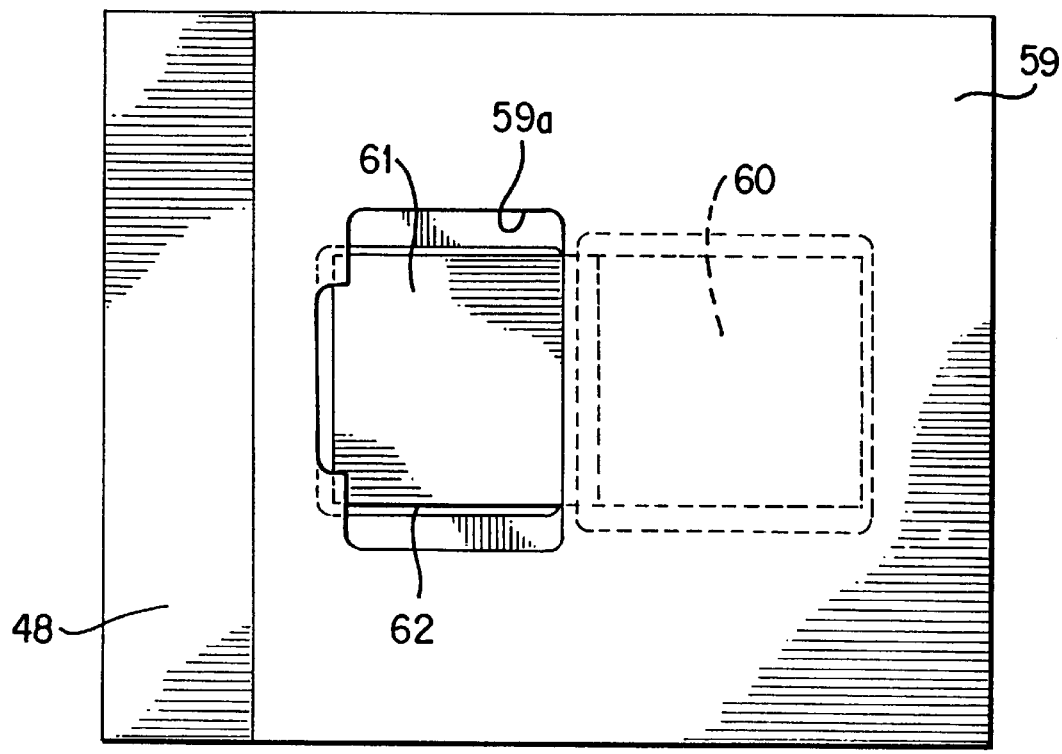

As shown in FIGS. 16(a) and 16(b), a concave resin cover 59 whose length×width×thickness is about 50 mm×about 50 mm×about 3 mm and the pressure cover 48 are screwed to each other. A piezoelectric element 60 whose length×width×thickness is about 20 mm×about 17 mm×about 1 mm is accommodated in the recess between the cover 59 and the pressure cover 48. One surface of the piezoelectric element 60 is secured to the cover 59. One end of the other surface of the piezoelectric element 60 is secured to one end of a porous plate 61 whose length×width×thickness is about 20 mm×about 17 mm×about 0.05 mm. Thus, the sprayer 32 is constituted. The porous plate 61 covers an open spray tank 62 which is a recess formed in the cover 48. The open spray tank 62 communicates with the acid liquid recovery channel 58 through an acid liquid outlet port 54. The piezoelectric element 60 is provided with an electrode made of gold on each surface. The electrodes are connected to the sprayer drive circuit of the controller 39 through terminals which are not shown and the wires 43c, 43d of the harness 44.

The porous plate 61 is constituted of an acid proof noble metal plate such as a platinum plate, a gold plate, a silver plate, etc. provided with numerous pores of about 0.01 mm to 0.02 mm diameter. The porous plate 61 may be constituted of a nickel plate provided with numerous pores of about 0.01 mm to 0.02 mm diameter whose whole surface including the inner surfaces of the pores is galvanized with a noble metal such as platinum, gold, silver, etc., titanium nitride, titanium carbide, etc. by physical vapour deposition or chemical vapour deposition, or coated with Teflon resin, etc. to increase its acid proof property. The joint between the piezoelectric element 60 and the porous plate 61 is coated with resin, etc. to increase the acid proof characteristics.

The distance between the porous plate 61 and the bottom of the open spray tank 62 opposite to the porous plate 61 is about 0.5 mm to about 1.5 mm. The distance is determined considering the fact that when the distance is too small, the porous plate adheres to the bottom of the open spray tank because of the surface tension of the acid liquid containing hypochlorous acid and stops vibration, while when the distance is too large, the added mass of the water increases to suppress the vibration of the porous plate.

The cover 59 is provided with an opening 59a opposite to the porous plate 61.

The hand switch 33 is connected to the CPU of the controller 39 through the wires 43e, 43f of the harness 44.

Figure 19:
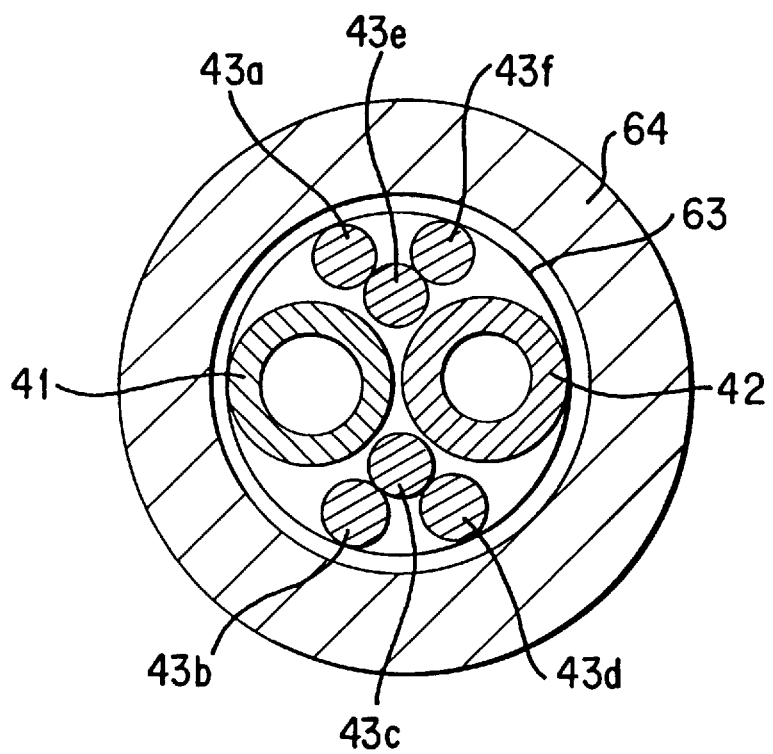
FIG. 19 is a sectional view of the harness of an apparatus for generating and spraying strong acid sterilizing liquid containing hypochlorous acid at a low concentration in accordance with an embodiment of the present invention.

As shown in FIG. 19, the harness 44 is constituted of the salt water supply tube 41, the discarded water discharge tube 42, wires 43a–43f, an inner sheath 63 for bundling the tubes and wires, and an outer sheath 64 for maintaining the shape of the harness 44. The inner diameter of the salt water supply tube 41 is set at about 1.4 mm. The inner diameter of the discarded water discharge tube 42 is set at about 1.0 mm. Thus, the ratio of the sectional area of the salt water supply tube 41 to that of the discarded water discharge tube 42 is 2 to 1. The inner diameters of the salt water supply tube 41 and the discarded water discharge tube 42 are determined considering the fact that when the diameters are too large, raising and lowering the electrolyzing and spraying unit 34 of this apparatus A during the operation causes a large variation in the load on the pump 37, the flow rate of the liquid, and the quantity of the sprayed mist, while when the inner diameters are too small, the flow resistance increases, the load on the pump 37 increases, and the use of a battery as the power supply becomes difficult.

The apparatus A for generating and spraying strong acid sterilizing liquid containing hypochlorous acid at a low concentration operates as follows.

The user grasps the electrolyzing and spraying unit 34 accommodated in the base unit 40 as shown in FIG. 15(a), detaches the electrolyzing and spraying unit 34 from the base unit 40 as shown in FIG. 15(b), brings the electrolyzing and spraying unit 34 close to an inflamed part of the skin suffering from atopy dermatitis, a part of the skin suffering from necrosis caused by diabetes, or a bedsore of bedridden old person, directs the acid mist supply opening 45a to the inflamed part, necrotic part, bedsore, etc. and pushes the hand switch 33 with a finger of the hand holding the electrolyzing and spraying unit 34 to start the controller 39.

The CPU of the controller 39 starts, the pump 37 is driven by the pump drive circuit, the electric power for the electrolysis is supplied to the non-barrier type electrolytic cell 31 from the electrolytic cell drive circuit through the harness 44, and the high frequency electric power for driving the piezoelectric element is supplied to the sprayer 32 from the sprayer drive circuit through the harness 44.

As indicated by arrows in FIG. 13, the pump 37 force feeds the salt water to the non-barrier type electrolytic cell 31 from the salt water tank 35 through the salt water supply tube 41 of the harness 44.

As indicated by arrows in FIG. 18, the salt water flowing into the salt water inlet port 52 of the non-barrier type electrolytic cell 31 passes into the salt water supply channel 56 and passes into the water flow channel 55.

The DC voltage is applied across the positive electrode plate 49 and the negative electrode plate 50 from the electrolytic cell drive circuit of the control unit 39. The salt water flowing in the water flow channel 55 is electrolyzed. Acid liquid containing hypochlorous acid is generated near the positive electrode plate 49 and alkaline liquid is generated near the negative electrode plate 50. The ratio of the quantity of the acid liquid containing hypochlorous acid generated near the positive electrode plate 49 to the quantity of the alkaline liquid generated near the negative electrode plate 50 is about 1 to 1.

As indicated by arrows in FIG. 18, the acid liquid containing hypochlorous acid generated near the positive electrode plate 49 and flowing along the positive electrode plate 49 passes into the acid liquid recovery channel 58 adjacent to the downstream end of the positive electrode plate 49 and extending over the whole width of the positive electrode plate 49, from the downstream portion of the water flow channel 55. The acid liquid containing hypochlorous acid passed into the acid liquid recovery channel 58 flows out of the non-barrier type electrolytic cell 31 through the acid liquid outlet port 54.

As indicated by arrows in FIG. 18, the alkaline liquid generated near the negative electrode plate 50 and flowing along the negative electrode plate 50 passes into the alkaline liquid recovery channel 57 from the downstream end of the water flow channel 55. The alkaline liquid passed into the alkaline liquid recovery channel 57 flows out of the non-barrier type electrolytic cell 31 through the alkaline liquid outlet port 53.

The acid liquid containing hypochlorous acid flowing out of the non-barrier type electrolytic cell 31 passes into the open spray tank 62 of the sprayer 32 and fills it. The acid liquid containing hypochlorous acid charged in the open spray tank 62 rises to one surface of the porous plate 61 covering the open end of the open spray tank 62. High frequency voltage is applied to the piezoelectric element 60 of the sprayer 32 from the sprayer drive circuit to cause the piezoelectric element 60 to expand and contract at high frequency. The porous plate 61 secured to the piezoelectric element 60 vibrates at high frequency. The acid liquid containing hypochlorous acid charged in the open spray tank 62 and in contact with one surface of the porous plate 61 covering the open end of the open spray tank 62, is atomized through the numerous micropores formed in the porous plate 61 and sprayed from the other surface of the porous plate 61 through the opening 59a of the cover 59 and the acid mist supply opening 45a of the case 45. Thus, an appropriate quantity of strong acid sterilizing liquid is applied to inflamed parts of the skin afflicted with atopy dermatitis, diabetic necrosis, or bedsores to kill MRSA on the diseased parts of the skin, thereby suppressing itch or suppuration of the diseased parts.

The alkaline liquid flowing out of the non-barrier type electrolytic cell 31 passes into the discarded water recovery tank 36 of the base unit 40 through the discarded water discharge tube 42 of the harness 44.

After the spraying is finished, the user pushes the hand-switch 33 to stop the operation of the controller. Then, the CPU of the controller 39 stops, the pump 37 stops, the non-barrier type electrolytic cell 31 stops, and the sprayer 32 stops. Following the stoppage of the pump 37, the supply of the salt water to the non-barrier type electrolytic cell 31 stops.

As necessary, the user replenishes the salt water tank 35 of the base unit 40 with salt water, discharges the alkaline liquid from the discarded water recovery tank 36, and replaces the battery of the DC power supply.

In the present apparatus A having the small sized electrolytic cell 31, it is possible to generate only the required quantity of strong acid liquid containing hypochlorous acid at a low concentration. In the present apparatus A wherein the electrolytic cell 31 and the sprayer 32 are integrated into the electrolyzing and spraying unit 34, the acid liquid containing hypochlorous acid generated by the electrolytic cell 31 can be immediately sprayed through the sprayer 32. Thus, the generated acid liquid containing hypochlorous acid is immediately used up without being stored so that the bactericidal activity of the sprayed acid liquid containing hypochlorous acid is always assured.

In the present apparatus A, the positive electrode plate 49 and the negative electrode plate 50 of the non-barrier type electrolytic cell 31 are disposed opposite to each other without a barrier between them. Thus, the distance between the electrodes is narrower than that in the conventional apparatus having a barrier type electrolytic cell, thereby decreasing the electric resistance of the salt water present between the electrodes. Thus, in the present apparatus A, the salt water can be electrolyzed with less consumption of electric power than that in the conventional apparatus having a barrier type electrolytic cell. In the present apparatus A, the non-barrier type electrolytic cell 31 can be made small by means of narrowing the distance between the electrodes, and the DC power supply 38 and the controller 39 can be made small by means of reducing the consumption of electric power. Thus, the present apparatus A is compact and portable and the electrolyzing and spraying unit 34 of the present apparatus A is palm sized. User can therefore freely take the present apparatus A to the place they want to use it. The user can grasp the palm sized electrolyzing and spraying unit 34 connected to the base unit 40 through the harness 44 and apply the acid liquid containing hypochlorous acid to any desired part of his or her body. Thus, the present apparatus A has high utility.

In the present apparatus A, the distance between the electrodes is narrowed so as to decrease the voltage applied across the electrodes, decrease the overvoltage at the positive electrode, increase the flow speed of the salt water in the water flow channel 55 between the electrodes, increase the number of hydroxide ions and hydrogen ions supplied to the surfaces of the electrodes, and cause the water flow in the water flow channel 55 to be a laminar flow. Thus, in the present apparatus A, the electrolysis of the salt water can be promoted while suppressing the excessive generation of chlorine and suppressing mixing of the water flow near the positive electrode plate 49 and the water flow near the negative electrode plate 50, whereby the strong acid sterilizing liquid which contains hypochlorous acid at a concentration of about 2 ppm, whose pH is 3 or less, and which is suitable for use on the human body can be obtained.

In the present apparatus A, the distance between the positive electrode plate 49 and the negative electrode plate 50 can be made narrow to decrease the voltage for the electrolysis and decrease the electric power for the electrolysis. Thus, in the present apparatus A, a battery can be used as the power supply for the electrolysis.

In the present apparatus A wherein the distance between the positive electrode plate 49 and the negative electrode plate 50 of the non-barrier type electrolytic cell 31 is about 0.2 mm to about 0.5 mm, a battery can be used as the power supply for the electrolysis, and the flow resistance of the water flow channel can be optimized to enable use of a battery as the power supply for the pump. The liquid which is sprayed from the electrolyzing and spraying unit 34 at the start of spraying is the electrolyzed water which has been residing in the open spray tank 62, acid liquid recovery channel 58 and the water flow channel 55 and has lost its bactericidal activity. In the present apparatus A wherein the distance between the positive electrode plate 49 and the negative electrode plate 50 of the non-barrier type electrolytic cell 31 is about 0.2 mm to about 0.5 mm, the volume of the water flow channel 55 is small and the quantity of the liquid which is sprayed from the electrolyzing and spraying unit 34 at the start of spraying is therefore small.

In the present apparatus A wherein the sprayer 32 is constituted by a piezoelectric element 60 and a porous plate 61 secured to the piezoelectric element 60 at its one end, the sprayer 32 can be downsized, the electric power consumption of the sprayer can be reduced, and a battery can be used as the power supply of the sprayer.

In the present apparatus A, the porous plate 61 of the sprayer 32 is made of noble metal such as platinum, gold, silver, etc., or the whole surface of the porous plate 61 including the inner surfaces of the pores is galvanized with noble metal such as platinum, gold, silver, etc., titanium nitride, titanium carbide, etc. by physical vapour deposition or chemical vapour deposition, or coated with Teflon resin, etc. The joint between the piezoelectric element 60 and the porous plate 61 is coated with resin. Thus, the sprayer 32 has high corrosion resistance against acid liquid containing hypochlorous acid.

In the present apparatus A wherein the sprayer 32 has the open spray tank 62 communicating with the acid water recovery channel 58 of the non-barrier type electrolytic cell 31 and the open end of the open spray tank 62 is covered with the porous plate 61, acid liquid containing hypochlorous acid flows into the open spray tank 62 through the acid liquid recovery channel 58 of the non-barrier type electrolytic cell 31, fills the open spraying tank 62, rises to one surface of the porous plate 61, and is sprayed from the other surface of the porous plate 61 through the numerous micropores formed in the porous plate 61. The acid liquid containing hypochlorous acid is supplied to one surface of the porous plate 61 and sprayed from the other surface of the porous plate 61. Thus, in the present apparatus A, the acid liquid containing hypochlorous acid can be sprayed more stably and in a better condition than in the conventional sprayer disclosed in Japanese Patent Laid-Open Publication Hei 4-150968 which has a piezoelectric element and a porous plate and wherein the liquid supplied to one surface of the porous plate is sprayed from the same surface so that the spray of the liquid is partially interrupted by the supplied liquid.

In the present apparatus A, the distance between the porous plate 61 of the sprayer 32 and the bottom of the open spray tank 62 opposite to the porous plate 61 is about 0.5 mm to about 1.5 mm. Therefore, the vibration of the porous plate 61 is not stopped by adherence thereof to the bottom of the open spray tank 62 due to the surface tension of the acid liquid and is not suppressed due to increase in the added mass of water.

In the present apparatus A wherein the ratio of the sectional area of the salt water supply tube 41 of the harness 44 to that of the discarded water discharge tube 42 of the harness 44 is set at 2 to1 considering the fact that the ratio of the quantity of the salt water supplied to the electrolytic cell 31 to that of the alkaline liquid flowing out of the electrolytic cell 31 is about 2 to 1, the flow of the salt water in the salt water supply tube 41 and the flow of the alkaline liquid in the discarded water discharge tube 42 are smooth.

In the present apparatus A wherein the base unit 40 has a compartment for accommodating the electrolyzing and spraying unit 34 and the harness 44, the whole apparatus becomes an integral body. Thus, downsizing and portability of the apparatus is promoted.

In the present apparatus A wherein an engaging apparatus is constituted by the groove 45b formed in the case 45 of the electrolyzing and spraying unit 34 and the flange 46a formed around the recess of the case 46, it is possible to spray the liquid with the electrolyzing and spraying unit 34 hooked on the base unit 40. Thus, it is possible to spray the sterilizing liquid on the diseased part without grasping the electrolyzing and spraying unit 34 with the hand.

In the present apparatus A wherein the electrolyzing and spraying unit 34 is provided with the hand switch 33 connected to the controller 39 of the base unit 40, the user can operate the apparatus A with the electrolyzing and spraying unit 34 held in the hand. Thus, the utility of the present apparatus A is increased.

In the present apparatus A, a battery type power source is used as the DC power supply 38. Thus, the present apparatus A can be used in a bathroom.

The present apparatus A was operated using four alkaline cells as the DC power supply (6 V). The pump 37 was operated under a constant voltage controlled to 4 V to supply salt water of a salt concentration of 400 ppm (mg/liter) to the electrolytic cell 31 at the flow rate of 40 to 50 cc/minute. The electrolytic cell 31 was operated under a constant electric current controlled to 0.15 A. The sprayer 32 was operated under a constant voltage controlled to 12 V to apply the piezoelectric element 60 with high frequency voltage of 20 to 45 kHz. Thus, strong acid liquid which contained hypochlorous acid at a low concentration of about 2 ppm and whose pH was 3 or less was sprayed from the electrolyzing and spraying unit 34 at the spraying rate of 20 to 25 cc/minute.

The present invention is not restricted to embodiments described in the foregoing.

Figure 11:
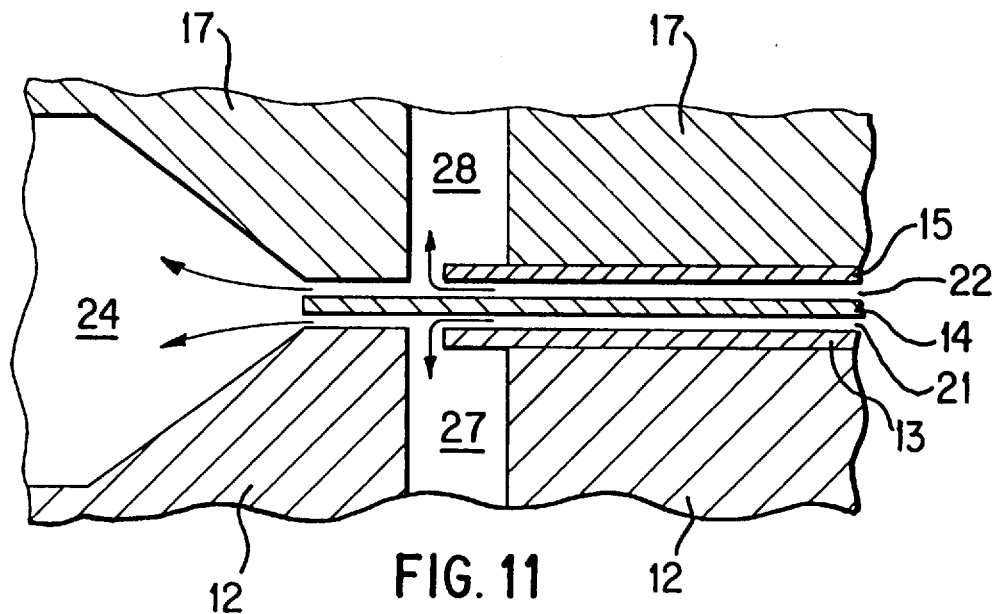
FIG. 11 is a view corresponding to FIG. 5 showing a variation of the non-barrier type electrolytic cell constituting an apparatus for generating strong acid sterilizing liquid containing hypochlorous acid at a low concentration in accordance with an embodiment of the present invention.
Figure 12:
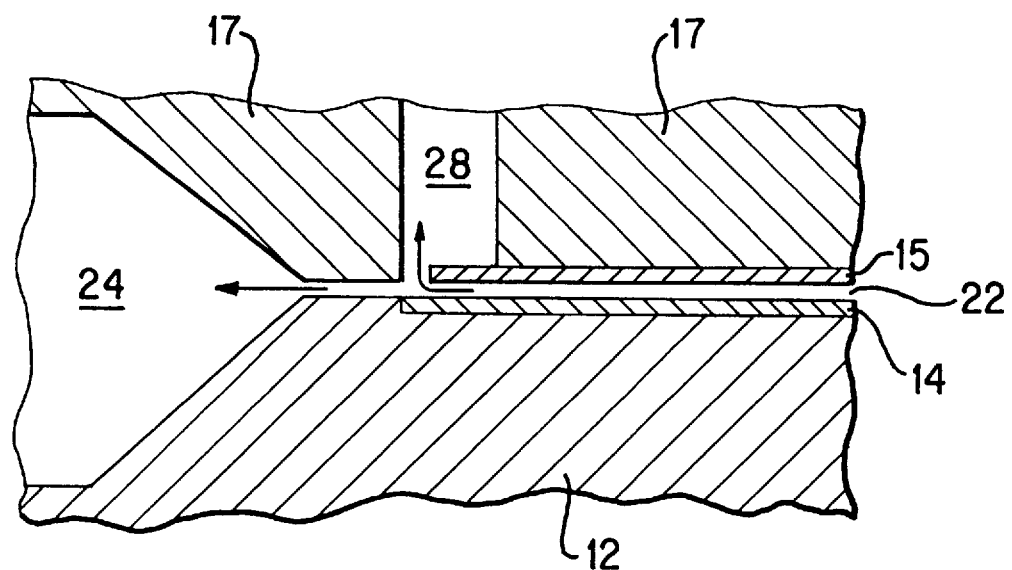
FIG. 12 is a view corresponding to FIG. 5 showing another variation of the non-barrier type electrolytic cell constituting an apparatus for generating strong acid sterilizing liquid containing hypochlorous acid at a low concentration in accordance with an embodiment of the present invention.

In the non-barrier type electrolytic cell 6 of the apparatus 1 for generating strong acid sterilizing liquid containing hypochlorous acid at a low concentration, it is possible, as shown in FIG. 11, to constitute the wall surfaces of the first water flow channel 21 upstream of the first acid liquid recovery channel 27 by the first positive electrode plate 13 and the negative electrode plate 14, and the wall surfaces of the second water flow channel 22 upstream of the second acid liquid recovery channel 28 by the second positive electrode plate 15 and the negative electrode plate 14. The wall surface of the first water flow channel 21 downstream of the first acid liquid recovery channel 27 can be constituted by the case 12 and the negative electrode plate 14, and the wall surface of the second water flow channel 22 downstream of the second acid liquid recovery channel 28 by the cover 17 and the negative electrode plate 14. As shown in FIG. 12, when the only water flow channel is the second water flow channel, the wall surface of the second water flow channel 22 upstream of the second acid liquid recovery channel 28 can be constituted by the negative electrode plate 14 and the second positive electrode plate 15 and the wall surface of the second water flow channel 22 downstream of the second acid liquid recovery channel 28 can be constituted by the case 12 and the cover 17.

In the non-barrier type electrolytic cell 6 of the apparatus 1 for generating strong acid sterilizing liquid containing hypochlorous acid at a low concentration, the positive electrode plates 13, 15 may be used as negative electrodes, the negative electrode plate 14 may be used as a positive electrode plate, the recovery channels 27, 28 may be used as alkaline liquid recovery channels, and the recovery channel 24 may be used as an acid liquid recovery channel.

In the apparatus 1 for generating strong acid sterilizing liquid containing hypochlorous acid at a low concentration, a cartridge having mesh filters or a cartridge having activated carbon may be used instead of the hollow fiber filtration film cartridge 5.

In the apparatus 1 for generating strong acid sterilizing liquid containing hypochlorous acid at a low concentration, the electrolysis may be operated under electric power control or electric current control from the viewpoint of controlling the quantity of electrolyzed water. However, it is fairly hard to obtain desired electrolyzed water only by electric current control because the properties of water in different places are different. According to the results of tests carried out by the inventors of the present invention, electric power control is preferable.

Figure 20:
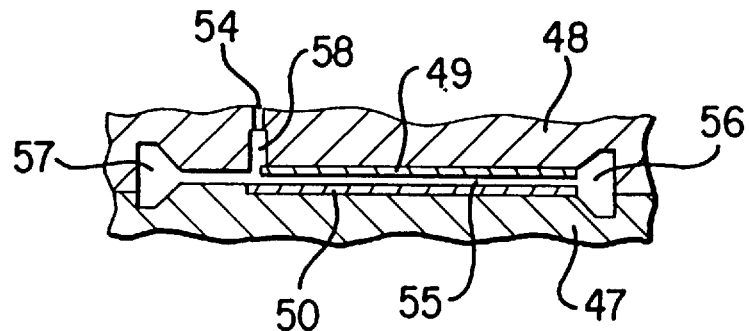
FIG. 20 is a sectional view of a variation of the electrolytic cell corresponding to FIG. 16($a$).
Figure 21:
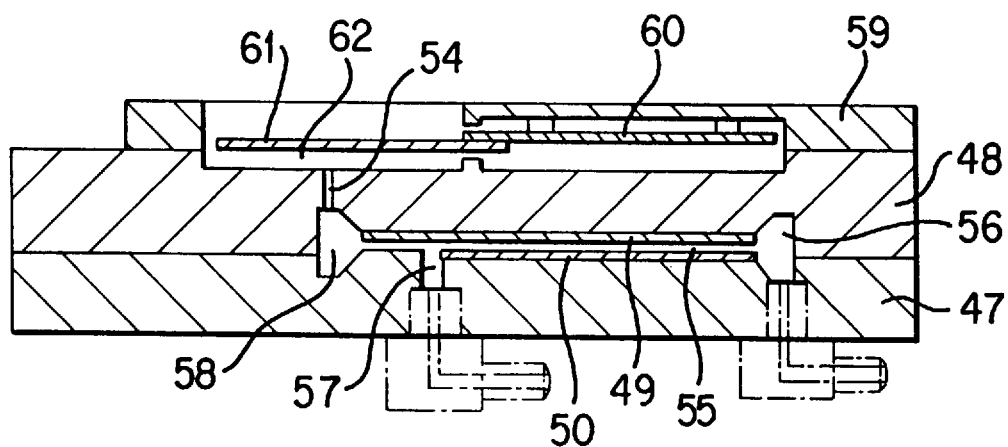
FIG. 21 is a sectional view of another variation of the electrolytic cell corresponding to FIG. 16($a$).

In the non-barrier electrolytic cell 31 of the apparatus A for generating and spraying strong acid sterilizing liquid containing hypochlorous acid at a low concentration, the portion of the water flow channel 55 downstream of the acid recovery channel 58 may be constituted by the case 47 and the cover 48 as shown in FIG. 20, or, as shown in FIG. 21, the acid recovery channel 58 may be placed in communication with the downstream end of the water flow channel 55 and the alkaline liquid recovery channel 57 may be formed adjacent to the downstream end of the negative electrode 50 at the downstream portion of the water flow channel 55.

Figure 22:
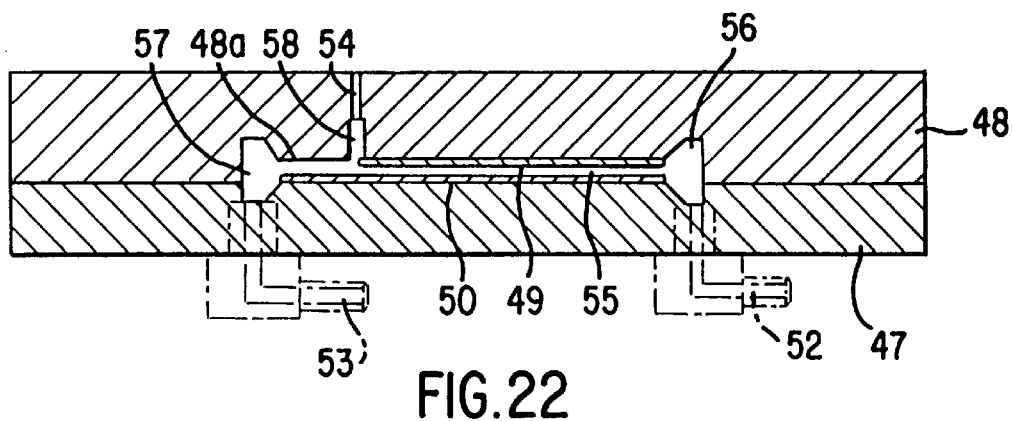
FIG. 22 is a sectional view of another variation of the electrolytic cell corresponding to FIG. 16($a$).
Figure 23:
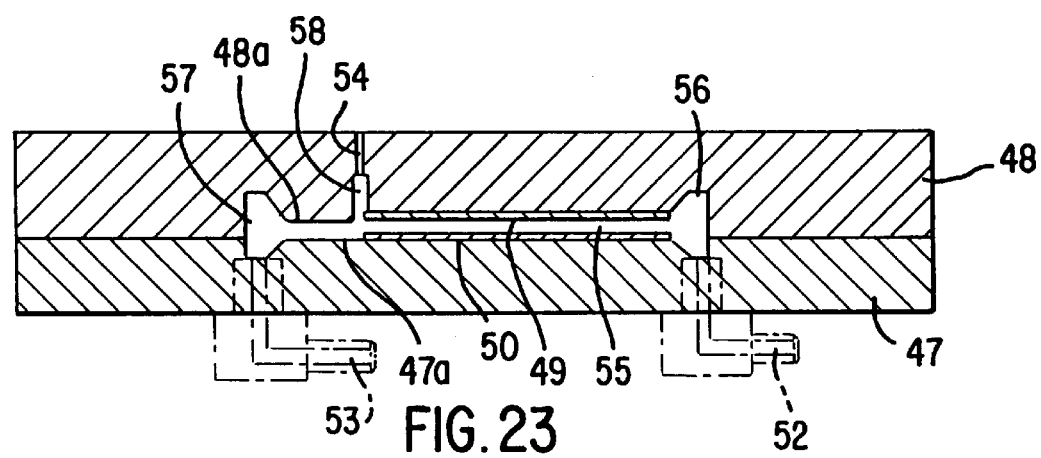
FIG. 23 is a sectional view of another variation of the electrolytic cell corresponding to FIG. 16($a$).

In the non-barrier electrolytic cell 31 of the apparatus A for generating and spraying strong acid sterilizing liquid containing hypochlorous acid at a low concentration, the flat surface 48a may, as shown in FIG. 22, be slightly offset from the positive electrode plate 49 in the direction apart from the negative electrode plate 50. The alkaline liquid near the negative electrode plate 50 flows along the negative electrode plate 50. Thus, the acid liquid near the positive electrode plate 49 passes into the acid liquid recovery channel 58. As shown in FIG. 23, the downstream end portion of the water flow channel 55 may be constituted by the flat surface 48a of the cover 48 extending flush with the positive electrode plate 49 and the flat surface 47a of the case 47 slightly offset from the negative electrode plate 50 in the direction apart from the positive electrode plate 49. The alkaline liquid near the negative electrode plate 50 flows along the negative electrode plate 50 and the flat surface 47a. Thus, the acid liquid near the positive electrode plate 49 passes into the acid liquid recovery channel 58.

In the apparatus A for generating and spraying strong acid sterilizing liquid containing hypochlorous acid at a low concentration, the pump 37, the electrolytic cell 31 and the sprayer 32 may be controlled according to a control program loaded in the memory of the controller 39 to continue spraying until a prescribed time passes after the stop of the electrolysis. Thus, the acid liquid containing hypochlorous acid which resides in the open spray tank 62 can be used up when the operation of the apparatus A is stopped. Thus, the quantity of the liquid sprayed at the start of the next operation of the apparatus A which has no bactericidal activity can be decreased.

In the apparatus A for generating and spraying strong acid sterilizing liquid containing hypochlorous acid at a low concentration, a polarity reverse circuit may be disposed in the electrolytic cell drive circuit. In this case, the non-barrier type electrolytic cell 31 is operated according to a control program loaded in the memory of the controller 39, the polarity of voltage applied across the electrodes of the non-barrier type electrolytic cell 31 is reversed just before the stop of the electrolysis, the electrolysis is continued for a short time, and the electrolysis is stopped. Thus, the adhesion of scale to the negative electrode plate 50 is suppressed.

In the apparatus A for generating and spraying strong acid sterilizing liquid containing hypochlorous acid at a low concentration, a compressor may be connected to the salt water tank 35 instead of the pump 37. In this case, the salt water pressurized by the compressor is force fed to the non-barrier type electrolytic cell 31. In this case, a closing valve controlled by the controller 39 or a manually operated closing valve is preferably disposed downstream of the salt water tank 35 to control the supply and the stop of the supply of the salt water to the non-barrier type electrolytic cell 31.

When the closing valve is disposed, the supply and the stop of the supply of the salt water to the non-barrier type electrolytic cell 31 can be carried out smoothly. When a manually operated closing valve is disposed, the start and the stop of the apparatus A may be operated by the closing valve.

In the apparatus A for generating and spraying strong acid sterilizing liquid containing hypochlorous acid at a low concentration, the harness 44 may be eliminated and the non-barrier type electrolytic cell 31 and the sprayer 32 may be disposed in the base unit 40. In this case, an acid mist supply opening of the base unit 40 communicating with the opening 59a of the sprayer 32 is directed to the diseased part during the spraying of the liquid.

In the apparatus A for generating and spraying strong acid sterilizing liquid containing hypochlorous acid at a low concentration, a mesh bag filled with Na—Ca substitute type ion exchange resin or H—Ca substitute type ion exchange resin may be disposed in the salt water tank 35. Thus, calcium ions are removed from the salt water and the adhesion of scale to the negative electrode plate 50 is suppressed.

The sprayer 32 may be eliminated from the apparatus A for generating and spraying strong acid sterilizing liquid containing hypochlorous acid at a low concentration and the apparatus A can be used as an apparatus for generating and discharging strong acid sterilizing liquid containing hypochlorous acid at a low concentration. In this case, the acid mist supply opening 45a of the case 45 becomes an acid liquid discharge port 45a. The acid liquid containing hypochlorous acid flowing out of the non-barrier type electrolytic cell 31 through the acid liquid outlet port 54 is dispensed from the acid liquid discharge port 45a of the case 45. The dispensed acid liquid containing hypochlorous acid can be directly applied to inflamed parts of the skin suffering from atopic dermatitis, or diabetic necrosis, or to bedsores of a bedridden old person, or be impregnated into absorbent cotton and applied to the diseased parts to sterilize MRSA propagated on the diseased parts of the skin, thereby suppressing itch or suppuration of the diseased parts.

The strong acid sterilizing liquid containing hypochlorous acid at a low concentration in accordance with the present invention can be applied to inflamed parts of the skin suffering from atopy dermatitis, or diabetic necrosis, or to bedsores of a bedridden old person to sterilize MRSA propagated on the diseased parts, thereby suppressing itch or suppuration of the diseased parts, or be applied to abrasions to kill Streptococus pyogenes present in the abrasions, thereby suppressing the suppuration of the injured part. The method and the apparatus in accordance with the present invention is useful for generating the strong acid sterilizing liquid containing hypochlorous acid at a low concentration.

The apparatus for generating and discharging strong acid sterilizing liquid containing hypochlorous acid at a low concentration in accordance with the present invention is compact and portable. The apparatus in accordance with the present invention can generate and dispense strong acid sterilizing liquid containing hypochlorous acid at a low concentration whose bactericidal activity is highly reliable.

TABLE 1

1   TEST CONDITIONS (1) TESTED STRAIN
    *Escherichia coli* IFO15034
(2) ADJUSTING OF THE LIQUID CONTAINING BACTERIA
    Bacteria cultured in SCD medium (NIPPON SEIYAKU CO. LTD.) for 16 hours were suspended in sterilized distilled water. (number of bacteria was $10^9$/ml to $10^{10}$/ml)
(3) MEDIUM FOR COUNTING THE NUMBER OF BACTERIA
    Normal agar medium (NIPPON SEIYAKU CO. LTD.)
(4) KINDS OF STERILIZING LIQUID

| chracteristic of the sterilizing liquid | pH | concentration of residual hypochlorous acid |
|---|---|---|
| sterilizing liquid 1 | 2.50 | 0.10 ppm |
| sterilizing liquid 2 | 2.51 | 0.22 ppm |
| sterilizing liquid 3 | 2.51 | 1.31 ppm |
| sterilizing liquid 4 | 2.41 | 11.8 ppm |
| sterilized water (for comparison) | 6.05 | 0.02 ppm |

TABLE 1-continued (5) TEST CONDITIONS

1) The liquid containing bacteria was diluted to contain $2 \times 10^5$/ml to $2 \times 10^6$/ml bacteria. 1 ml of the diluted liquid was poured in 1 ml of the sterilizing liquid to adjust the number of bacteria in the sterilizing liquid mixed with the diluted liquid to about $10^5$/ml to $10^6$/ml, and the diluted liquid was contacted with the sterilizing liquid for about 1 second.
2) Just after the passage of 1 second, the tested liquid was neutralized by addition of aqueous solution of sodium thiosulfate.
3) The neutralized tested liquid was stepwise diluted by adding physiological salt water. The number of surviving bacteria was counted by the smear method (35°C., 48 hours of culture).

TABLE 2

| | characteristic of sterilizing liquid | | number of bacteria before the contact | number of bacteria after the contact |
|---|---|---|---|---|
| | pH | concentration of residual hypochlorous acid | | |
| sterilizing liquid 1 | 2.50 | 0.10 ppm | $1.0 \times 10^6$ | $1.1 \times 10^5$ |
| sterilizing liquid 2 | 2.51 | 0.22 ppm | $1.0 \times 10^6$ | $2.4 \times 10^3$ |
| sterilizing liquid 3 | 2.51 | 1.31 ppm | same as above | <50 |
| sterilizing liquid 4 | 2.41 | 11.8 ppm | same as above | <50 |
| sterilized water (for comparison) | 6.05 | 0.02 ppm | same as above | $1.0 \times 10^6$ |

TABLE 3

| | CONTACT TIME (SECOND) | | | | | | |
|---|---|---|---|---|---|---|---|
| TESTED BACTERIA | 0 | 5 | 10 | 30 | 60 | 300 | |
| Escherichia coli | $1.8 \times 10^6$ (6.26) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) 99.9999 or more | ← number of bacteria/ml<br>← log(number of bacteria/ml)<br>← sterilizing rate |
| Staphylococcus aureus | $6.9 \times 10^6$ (6.84) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| Streptococcus pyrogenes | $6.0 \times 10^5$ (5.78) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| Pseudomonas aeruginosa | $1.0 \times 10^6$ (6.00) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| MRSA (Methicillin-Resistant Stapyylococcus Aureus) | $3.4 \times 10^6$ (6.51) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| Salmonella typhimurium | $5.1 \times 10^6$ (6.71) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| Bacillus subtilis | $6.7 \times 10^5$ (5.83) | $4.1 \times 10^3$ (3.61) 99% or more | $3.1 \times 10^3$ (3.49) same as left | $4.7 \times 10^3$ (<3.67) same as left | $4.4 \times 10^3$ (3.64) same as left | $2.7 \times 10^3$ (3.43) same as left | |

TABLE 4

| TESTED BACTERIA | CONTACT TIME (SECOND) | | | | | | |
| --- | --- | --- | --- | --- | --- | --- | --- |
| | 0 | 5 | 10 | 30 | 60 | 300 | |
| Escherichia coli | $3.7 \times 10^6$ (6.57) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) 99.9999 or more | ← number of bacteria/ml<br>← log(number of bacteria/ml)<br>← sterilizing rate |
| Staphylococcus aureus | $9.1 \times 10^6$ (5.96) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| Streptococcus pyrogenes | $3.0 \times 10^6$ (6.48) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| Pseudomonas aeruginosa | $2.1 \times 10^5$ (5.32) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| MRSA (Methicillin-Resistant Stapyylococcus Aureus) | $3.2 \times 10^6$ (6.51) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| Salmonella typhimurium | $4.3 \times 10^5$ (5.63) | $<1.0 \times 10^2$ (<2.00) 99.9999 or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |
| Bacillus subtilis | $4.0 \times 10^5$ (5.60) | $<1.0 \times 10^2$ (<2.00) 99% or more | $<1.0 \times 10^2$ (<2.00) same as left | $<1.0 \times 10^2$ (<2.00) same as left | $<1.0 \times 10^2$ (<2.00) same as left | $<1.0 \times 10^2$ (<2.00) same as left | |

TABLE 5

| | pH | | |
| --- | --- | --- | --- |
| HClO | 2.3 | 2.5 | 7.0 |
| 0.5 | ◉ | ◉ | ◉ |
| 1.0 | — | — | ◉ |
| 1.5 | — | — | ◉ |
| 2.0 | ◉ | ◉ | ◉ |

NOTES
◉: sterilizing rate 99.99% or more ($10^6 \to 10^2$ or less)
◎: sterilizing rate 99.99% ($10^6 \to 10^2$)
○: sterilizing rate 99.9% ($10^6 \to 10^3$)
Δ: sterilizing rate 99% or less ($10^6 \to 10^4$ or more)

TABLE 6

| | pH | | | | |
| --- | --- | --- | --- | --- | --- |
| HClO | 2.5 | 2.7 | 3.0 | 5.0 | 7.0 |
| 0.5 | ○ | ○ | ○ | Δ | Δ |
| 1.0 | ◎ | ◎ | ◎ | Δ | Δ |
| 1.5 | ◉ | ◉ | ◎ | ○ | ○ |
| 2.0 | ◉ | ◉ | ◎ | ◎ | ○ |

NOTES
◉: sterilizing rate 99.99% or more ($10^6 \to 10^2$ or less)
◎: sterilizing rate 99.99% ($10^6 \to 10^2$)
○: sterilizing rate 99.9% ($10^6 \to 10^3$)
Δ: sterilizing rate 99% or less ($10^6 \to 10^4$ or more)

We claim:

1. A method for generating acid sterilizing liquid comprising the steps of:

providing first and second adjacent, parallel flat wall surfaces arranged to form a channel between them having a flow direction, wherein there is no barrier between the first and second wall surfaces;

providing a positive electrode plate to form at least part of said first wall surface;

providing a slit in the first wall surface at right angles to the flow direction;

providing a negative electrode plate to form at least part of the other of said wall surfaces;

passing salt water through the channel;

electrolyzing the salt water passing through the channel; and taking a layer of acid liquid from said electrolyzed salt water passing through the channel through the slit to provide acid sterilizing liquid.

2. A method according to claim 1, wherein a distance between the first and second wall surfaces is between about 0.2 mm and about 0.5 mm.

3. A method according to claim 1, further comprising the step of controlling electric power during said step of electrolyzing.

4. A method according to claim 1, further comprising the step of controlling a salt concentration of said salt water.

5. A method for generating acid sterilizing liquid comprising the steps of:

providing first and second adjacent, parallel flat wall surfaces arranged to form a channel between them having a flow direction, wherein there is no barrier between the first and second wall surfaces;

providing a positive electrode plate to form at least part of said first wall surface;

providing a negative electrode plate to form at least part of the other of said wall surfaces;

providing a slit in the second wall surface at right angles to the flow direction;

passing salt water through the channel;

electrolyzing the salt water passing through the channel, generating a layer of acid liquid proximal to the positive electrode, and a layer of alkaline liquid proximal to the negative electrode; and taking the layer of alkaline liquid through the slit, whereby acid sterilizing liquid is provided by said channel.

6. A method according to claim 5, wherein a distance between the first and second wall surfaces is between about 0.2 mm and about 0.5 mm.

7. A method according to claim 5, further comprising the step of controlling electric power during said step of electrolyzing.

8. A method according to claim 5, further comprising the step of controlling a salt concentration of said salt water.

9. An apparatus for generating acid sterilizing liquid comprising:

an electrolytic cell having first and second adjacent wall surfaces forming a first channel therebetween having a flow direction, wherein there is no barrier between the first and second wall surfaces, the first wall surface having a slit formed therein at right angles to the flow direction constructed to remove a layer of acid liquid proximal to the first wall surface, a positive electrode plate forming at least part of the first wall surface, a negative electrode plate forming at least part of the second wall surface;

a second channel communicating with the slit to remove acid liquid proximal to the first wall surface;

a third channel communicating with the first channel downstream of the slit to remove alkaline liquid proximal to the second wall surface;

a salt water tank;

a fourth channel communicating between the salt water tank and the first channel to supply salt water from the tank to the first channel; and a DC power supply operatively connected to the positive and negative electrodes to apply a voltage across the electrodes.

10. An apparatus according to claim 9, wherein a distance between said first and second wall surfaces is between about 0.2 mm and about 0.5 mm.

11. An apparatus according to claim 9, further comprising a controller operably connected to the electrode plates, which controls electric power delivered to said electrolytic cell.

12. An apparatus according to claim 9, further comprising a controller operable connected to the fourth channel, which controls a salt concentration of salt water supplied to said first channel.

13. An apparatus for generating acid sterilizing liquid comprising:

an electrolytic cell having first and second adjacent wall surfaces forming a first channel therebetween having a flow direction, wherein there is no barrier between the first and second wall surfaces, the second wall surface having a slit formed therein at right angles to the flow direction constructed to remove a layer of alkaline liquid proximal to the second wall surface, a positive electrode plate forming at least part of the first wall surface, a negative electrode plate forming at least part of the second wall surface;

a second channel communicating with the slit to remove alkaline liquid proximal to the second wall surface;

a third channel communicating with the first channel downstream of the slit to remove acid liquid proximal to the second wall surface;

a salt water tank;

a fourth channel communicating between the salt water tank and the first channel to supply salt water from the tank to the first channel; and a DC power supply operatively connected to the positive and negative electrodes to apply a voltage across the electrodes.

14. An apparatus according to claim 13, wherein a distance between said first and second wall surfaces is between about 0.2 mm and about 0.5 mm.

15. An apparatus according to claim 13, further comprising a controller operably connected to the electrode plates, which controls electric power delivered to said electrolytic cell.

16. An apparatus according to claim 13, further comprising a controller operable connected to the fourth channel, which controls a salt concentration of salt water supplied to said first channel.

17. An apparatus for generating and dispensing acid sterilizing liquid comprising:

a non-barrier electrolytic cell having first and second adjacent wall surfaces forming a first channel therebetween having a flow direction, wherein there is no barrier between the first and second wall surfaces, a positive electrode plate forming at least part of the first wall surface, a negative electrode plate forming at least part of the second wall surface, the first wall surface having a slit formed therein at right angles to the flow direction constructed to remove a layer of acidic liquid proximal to the first wall surface;

a second channel communicating with the slit to remove acid liquid proximal to the first wall surface;

a third channel communicating with the first channel downstream of the slit to remove alkaline liquid proximal to the second wall surface;

a salt water tank;

a fourth channel communicating between the salt water tank and the first channel to supply salt water from the tank to the first channel;

a supply device which feeds salt water from the salt water tank to the non-barrier electrolytic cell;

a recovery tank connected to the third channel to recover the alkaline liquid;

a DC power supply operatively connected to the positive and negative electrodes to apply a voltage across the electrodes; and a controller operatively connected to control the operation of the DC power supply and the supply device.

18. An apparatus according to claim 17, wherein a distance between said first and second wall surfaces is between about 0.2 mm and about 0.5 mm.

19. An apparatus according to claim 17, wherein a ration of a cross sectional area of fourth channel to the third channel is 2 to 1.

20. An apparatus according to claim 17, further comprising a palm size electrolytic cell unit including said electrolytic cell, a base unit comprising the salt water tank, the recovery tank and the supply device, the DC power supply and the controller, and a harness connecting the cell unit with the base unit, and including the third and fourth channels.

21. An apparatus according to claim 20, wherein the base unit further comprises a compartment which receives the cell unit and harness.

22. An apparatus according to claim 20, further comprising means for hooking the cell unit on the base unit.

23. An apparatus according to claim 20, further comprising a hand switch disposed on the harness and operably connected to the controller.

24. An apparatus according to claim 20, wherein said supply device is a pump operably connected to the fourth channel.

25. An apparatus according to claim 20, wherein said supply device is a compressor operably connected to pressurize liquid in the salt water tank.

26. An apparatus according to claim 25, further comprising a closing valve connected to control closing of the fourth channel.

27. An apparatus according to claim 17, further comprising a switching device which reverses a polarity of voltage applied across said electrodes.

28. An apparatus according to claim 17, further comprising an ion exchange resin disposed in said salt water tank.

29. An apparatus according to claim 17, wherein said DC power supply is a battery.

30. An apparatus according to claim 17, further comprising a spray device operably connected to the second channel.

31. An apparatus according to claim 30, wherein the sprayer further comprises a porous plate and a piezoelectric element operable connected to the porous plate.

32. An apparatus according to claim 31, wherein said porous plate comprises acid resistant material.

33. An apparatus according to claim 31, wherein an entire surface area including pores is coated with acid resistant material.

34. An apparatus according to claim 31, further comprising a spray tank disposed between an outlet of the second channel and the porous plate.

35. An apparatus according to claim 34, wherein said spray tank has a depth of between about 0.5 mm and about 1.5 mm.

36. An apparatus for generating and dispensing acid sterilizing liquid comprising:
- a non-barrier electrolytic cell having first and second adjacent wall surfaces forming a first channel therebetween having a flow direction, wherein there is no barrier between the first and second wall surfaces, a positive electrode plate forming at least part of the first wall surface, a negative electrode plate forming at least part of the second wall surface, the second wall surface having a slit formed therein at right angles to the flow direction constructed to remove a layer of alkaline liquid proximal to the second wall surface;
- a second channel communicating with the slit to remove alkaline liquid proximal to the second wall surface;
- a third channel communicating with the first channel downstream of the slit to remove acid liquid proximal to the first wall surface;
- a salt water tank;
- a fourth channel communicating between the salt water tank and the first channel to supply salt water from the tank to the first channel;
- a supply device which feeds salt water from the salt water tank to the first channel of the non-barrier electrolytic cell;
- a recovery tank connected to the second channel to recover the alkaline liquid;
- a DC power supply operatively connected to the positive and negative electrodes to apply a voltage across the electrodes; and
- a controller operatively connected to control the operation of the DC power supply and the supply device.

37. An apparatus according to claim 36, wherein a distance between said first and second wall surfaces is between about 0.2 mm and about 0.5 mm.

38. An apparatus according to claim 36, wherein a ration of a cross sectional area of fourth channel to the second channel is 2 to 1.

39. An apparatus according to claim 36, further comprising a palm size electrolytic cell unit including said electrolytic cell, a base unit comprising the salt water tank, the recovery tank and the supply device, the DC power supply and the controller, and a harness connecting the cell unit with the base unit, and including the second and fourth channels.

40. An apparatus according to claim 39, wherein the base unit further comprises a compartment which receives the cell unit and harness.

41. An apparatus according to claim 39, further comprising means for hooking the cell unit on the base unit.

42. An apparatus according to claim 39, further comprising a hand switch disposed on the harness and operably connected to the controller.

43. An apparatus according to claim 39, wherein said supply device is a pump operably connected to the fourth channel.

44. An apparatus according to claim 39, wherein said supply device is a compressor operably connected to pressurize liquid in the salt water tank.

45. An apparatus according to claim 44, further comprising a closing valve connected to control closing of the fourth channel.

46. An apparatus according to claim 36, further comprising a switching device which reverses a polarity of voltage applied across said electrodes.

47. An apparatus according to claim 36, further comprising an ion exchange resin disposed in said salt water tank.

48. An apparatus according to claim 36, wherein said DC power supply is a battery.

49. An apparatus according to claim 36, further comprising a spray device operably connected to the third channel.

50. An apparatus according to claim 49, wherein the sprayer further comprises a porous plate and a piezoelectric element operable connected to the porous plate.

51. An apparatus according to claim 50, wherein said porous plate comprises acid resistant material.

52. An apparatus according to claim 50, wherein an entire surface area including pores is coated with acid resistant material.

53. An apparatus according to claim 50, further comprising a spray tank disposed between an outlet of the second channel and the porous plate.

54. An apparatus according to claim 53, wherein said spray tank has a depth of between about 0.5 mm and about 1.5 mm.

* * * * *